US012576157B2

(12) United States Patent
Brown et al.

(10) Patent No.: US 12,576,157 B2
(45) Date of Patent: *Mar. 17, 2026

(54) PEPTIDE SAPORIN CONJUGATE FOR THE TREATMENT OF CANCER

(71) Applicant: SRI International, Menlo Park, CA (US)

(72) Inventors: Kathlynn C. Brown, Staunton, VA (US); Curtis Allred, Menlo Park, CA (US); Michael McGuire, Harrisonburg, VA (US)

(73) Assignee: SRI International, Menlo Park, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 18/352,791

(22) Filed: Jul. 14, 2023

(65) Prior Publication Data

US 2024/0024495 A1 Jan. 25, 2024

Related U.S. Application Data

(63) Continuation of application No. 16/629,803, filed as application No. PCT/US2018/041412 on Jul. 10, 2018, now Pat. No. 11,738,089.

(60) Provisional application No. 62/530,674, filed on Jul. 10, 2017.

(51) Int. Cl.
| | |
|---|---|
| *A61K 47/64* | (2017.01) |
| *A61K 38/16* | (2006.01) |
| *A61K 45/06* | (2006.01) |
| *A61K 47/60* | (2017.01) |
| *A61P 35/00* | (2006.01) |

(52) U.S. Cl.
CPC ........ *A61K 47/6415* (2017.08); *A61K 38/168* (2013.01); *A61K 45/06* (2013.01); *A61K 47/60* (2017.08); *A61P 35/00* (2018.01)

(58) Field of Classification Search
CPC ................................................ A61K 47/6415
See application file for complete search history.

(56) References Cited

U.S. PATENT DOCUMENTS

| | | | |
|---|---|---|---|
| 8,241,623 B1 | 8/2012 | Bermudes | |
| 8,524,220 B1 | 9/2013 | Bermudes | |
| 8,623,350 B1 | 1/2014 | Bermudes | |
| 9,068,187 B1 | 6/2015 | Bermudes | |
| 10,925,960 B2* | 2/2021 | Brown ..................... | C12N 7/00 |
| 11,738,089 B2* | 8/2023 | Brown ................. | C07K 14/415 |
| | | | 424/183.1 |
| 11,965,004 B2* | 4/2024 | Brown ............... | G01N 33/5076 |
| 2005/0288492 A1 | 12/2005 | Rabbitts et al. | |
| 2006/0239968 A1 | 10/2006 | Arap et al. | |
| 2008/0206136 A1 | 8/2008 | Greene et al. | |
| 2009/0110662 A1 | 4/2009 | Breitenkamp et al. | |
| 2010/0247589 A1 | 9/2010 | Fahnestock et al. | |
| 2011/0281354 A1 | 11/2011 | Stayton et al. | |
| 2012/0141478 A1 | 6/2012 | Coupade | |
| 2012/0208742 A1 | 8/2012 | Primiano et al. | |
| 2012/0283410 A1 | 11/2012 | Mirosevich et al. | |
| 2014/0022045 A1 | 1/2014 | Jang et al. | |
| 2014/0094404 A1* | 4/2014 | Villaverde Corrales ................... | |
| | | | C12N 15/62 |
| | | | 435/375 |
| 2015/0071862 A1 | 3/2015 | Sabatino et al. | |
| 2015/0203557 A1 | 7/2015 | Debinski et al. | |
| 2015/0315594 A1 | 11/2015 | Prakash et al. | |
| 2016/0310607 A1 | 10/2016 | Ryves | |
| 2017/0281752 A1 | 10/2017 | Brown et al. | |
| 2019/0077752 A1* | 3/2019 | Lerchen ............... | C07D 401/12 |
| 2022/0227823 A1 | 7/2022 | Brown et al. | |

FOREIGN PATENT DOCUMENTS

| | | | | |
|---|---|---|---|---|
| AU | 2018301651 | 1/2019 | | |
| AU | 2018301804 | 1/2019 | | |
| CN | 1816352 A | 8/2006 | | |
| CN | 101724073 A | 6/2010 | | |
| CN | 111278847 | 6/2020 | | |
| CN | 111417646 | 7/2020 | | |
| EP | 2018831080 | 2/2020 | | |
| EP | 2018831318 | 10/2020 | | |
| JP | 2014508515 A | 4/2014 | | |
| JP | 2020501231 | 1/2020 | | |
| JP | 2020501210 | 10/2020 | | |
| WO | 2009089186 A2 | 7/2009 | | |
| WO | WO 2012040513 | * | 3/2012 | |
| WO | WO-2012040513 A1 | * | 3/2012 | ........... A61K 31/353 |
| WO | 2012095527 A1 | 7/2012 | | |
| WO | 2012177868 A1 | 12/2012 | | |
| WO | 2016022597 A1 | 2/2016 | | |
| WO | 2016100748 A1 | 6/2016 | | |
| WO | 2018114798 A1 | 6/2018 | | |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

(Continued)

*Primary Examiner* — Nizal S Chandrakumar

(74) *Attorney, Agent, or Firm* — Dicke, Billig & Czaja, PLLC

(57) ABSTRACT

Disclosed herein, are compositions comprising one or more a molecular guidance system (MGS) peptides and a cytotoxic agent. Also described herein, are methods of administering the compositions to patients with cancer.

8 Claims, 33 Drawing Sheets

Specification includes a Sequence Listing.

(56)             References Cited

FOREIGN PATENT DOCUMENTS

WO        2019014190  A1    1/2019
WO        2019014199  A1    1/2019
WO        2004003170  A2    1/2024

OTHER PUBLICATIONS

"Find ETDs Home » Thesis Resources » Find ETDs" Online: "https://ndltd.org/thesis-resources/find-etds/" Accessed Jan. 31, 2023.*

Irwin "ZINC—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

STN Registry/Zregistry (CAS Registrysm) Sep. 2016 2 pages.*

Umlauf, Bioconjugate Chemistry (2014), 25(10), 1829-1837.*

Bruno , Ther Deliv. Nov. 2013 ; 4(11): 1443-1467.*

Drazic, Biochimica et Biophysica Acta (BBA)—Proteins and Proteomics, vol. 1864, Issue 10, Oct. 2016, pp. 1372-1401.*

Feldman, Understanding 'Evergreening' : Making Minor Modifications Of Existing Medications To Extend Protections, Health Affairs Jun. 2022 41:6, 801-804.*

Dwivedi, Evergreening: A deceptive device in patent rights, Technology in Society 32 (2010) 324-330.*

McGuire, Scientific Reports 4 : 4480, 1-11, 2014.*

Rabideau, ACS Cent. Sci. 2015, 1, 423-430.*

Venkatesh et al., "Role of the Development Scientist in Compound Lead Selection and Optimization", J. Pharm. Sci. 89, 145-154 (2000) pp. 145-154.

J. G. Cannon, "Analog Design" Chapter Nineteen in Burger's Medicinal Chemistry and Drug Discovery, Fifth Edition, vol. I: Principles and Practice, Wiley Interscience 1995, pp. 783-802.

Giansanti, F. et al. "PDZ domain in the engineering and production of a saporin chimeric toxin as a tool for targeting cancer cells: PDZ-mediated targeting of saporin toxin", Journal of Cellular Biochemistry, vol. 116, No. 7, Jul. 1, 2015; pp. 1256-1266.

Kuang, H. et al. "The design of peptide-amphiphiles as functional ligands for liposomal anticancer drug and gene delivery", Advanced drug delivery reviews, vol. 110, Aug. 2016, p. 80-101.

Lim, K.J. et al. "A cancer specific cell-penetrating peptide, BR2, for the efficient delivery of an scFv into cancer cells", Jun. 1, 2013, PLOS One, vol. 8, No. 6, p. e66084.

Mcguire, et al. Identification and characterization of a suite of tumor targeting peptides for non-small cell lung cancer. Scientific Reports, Mar. 27, 2014, vol. 4, Article 4480, pp. 1-11.

Umlauf, BJ. et al. "Modular three-component delivery system facilitates HLA class I antigen presentation and CD8+ T-cell activation against tumors", Molecular Therapy, vol. 23, No. 6, Jun. 2015, pp. 1092-1102.

Umlauf, BJ. et al. "Identification of a novel lysosomal trafficking peptide using phage display biopanning coupled with endocytic selection pressure", Bioconjugate Chemistry, vol. 25, No. 10, Oct. 2014, pp. 1829-1837.

Zhou, et al., "Cell-specific delivery of a chemotherapeutic to lung cancer cells", Journal of the American Chemical Society, vol. 126, No. 48, Dec. 8, 2004, pp. 15656-15657.

International Search Report and Written Opinion were mailed on Dec. 4, 2018 by the International Searching Authority for International Application No. PCT/US2018/041412, filed on Jul. 10, 2018 and published as WO/2019/014199 on Jan. 17, 2019 (Applicant—SRI International) (14 Pages).

International Preliminary Report on Patentability was mailed on Jan. 14, 2020 by the International Searching Authority for International Application No. PCT/US2018/041412, filed on Jul. 10, 2018 and published as WO/2019/014199 on Jan. 17, 2019 (Applicant—SRI International) (9 Pages).

Brown, "Pettidic Tumor Targeting Agents the Road from Phage Display Peptide Selections to Clinical Applications", Currnet Pharmaceutical Design, 16(9):1040-1054 (Mar. 1, 2010).

Guthi et al., "MRI-Visible Micellar Nanomedicine for Targeted Drug Delivery to Lung Cancer Cells", Mol Pharm, 7(1):32-40 (Feb. 1, 2010).

Kuzmin et al., "Effect of N- and C-Terminal Modifications on Cytotoxic Properties of Antimicrobial Peptide Tachyplesin I", Bulletin of Experimental Biology and Medicine, 162(6):754-757— (Apr. 20, 2017).

Singh et al., "Dimerization of a Phage-Display Selected Peptide for Imaging of $\alpha v \beta$—Integrin: Two Approaches to the Multivalent Effect", Theranostics, 4(7): 745-760 (May 15, 2014).

Tai et al., "Functional peptides for 1-14 siRNA delivery", Advanced Drug Delivery Reviews, 110-111:157-168 (Aug. 13, 2016).

* cited by examiner

Half Maximal Internalization

26 ± 4.5 nM

Peptide Internalization

Normal Flow
Cytometry 1 hr incubation
in the cold

Trypsin cuts up cell
surface proteins and
lifts cells off plate

Lifts cells but
dosen't cut proteins

Lifts cells but
dosen't cut proteins

| | IC50 |
|---|---|
| Trial 1 | 4.04e-9 |
| Trial 2 | 3.97e-9 |
| Trial 3 | 8.28e-9 |
| Average | 5.43e-9 ±2.47e-9 |

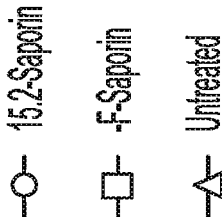
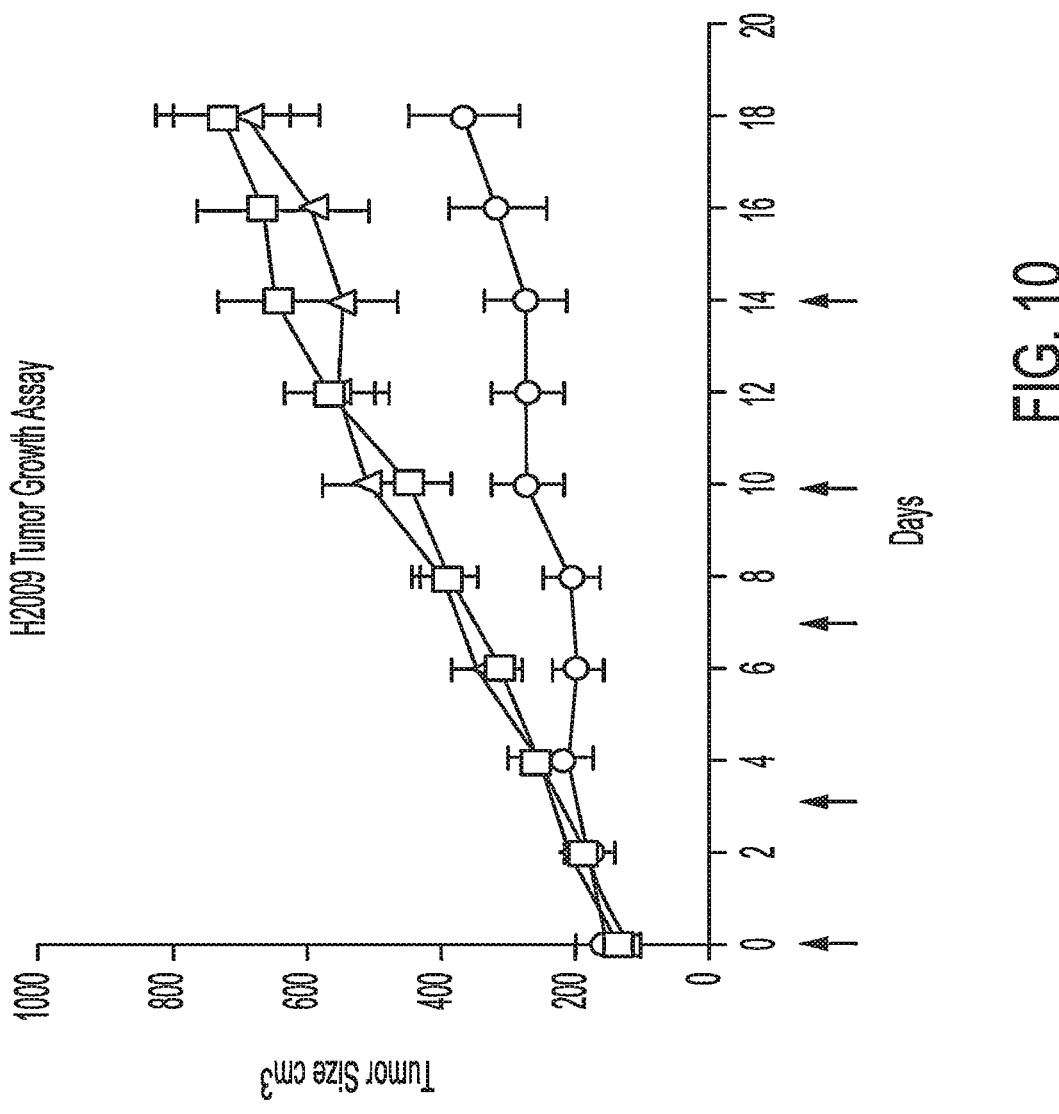
FIG. 10

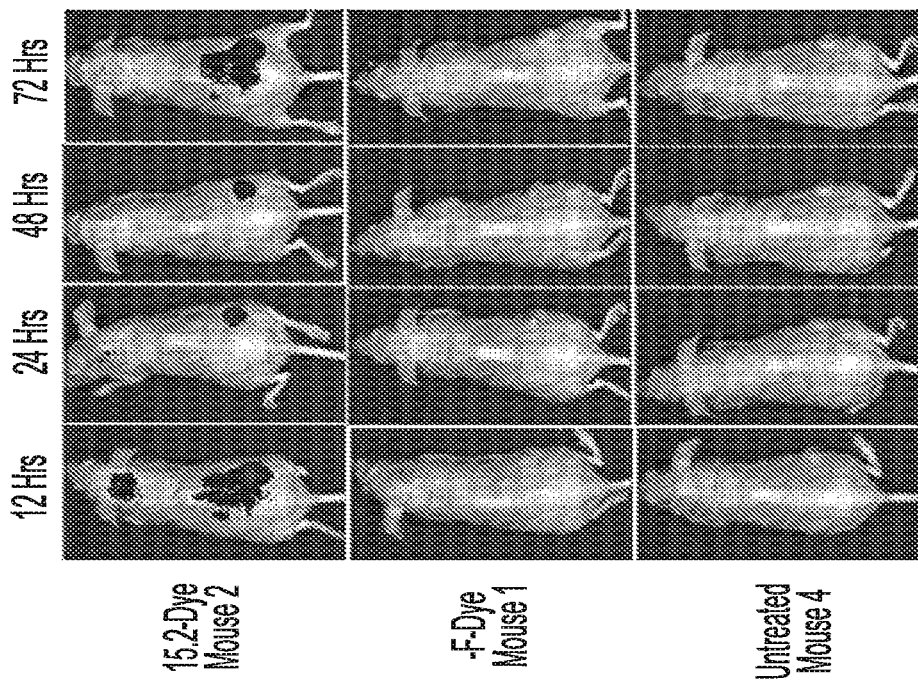
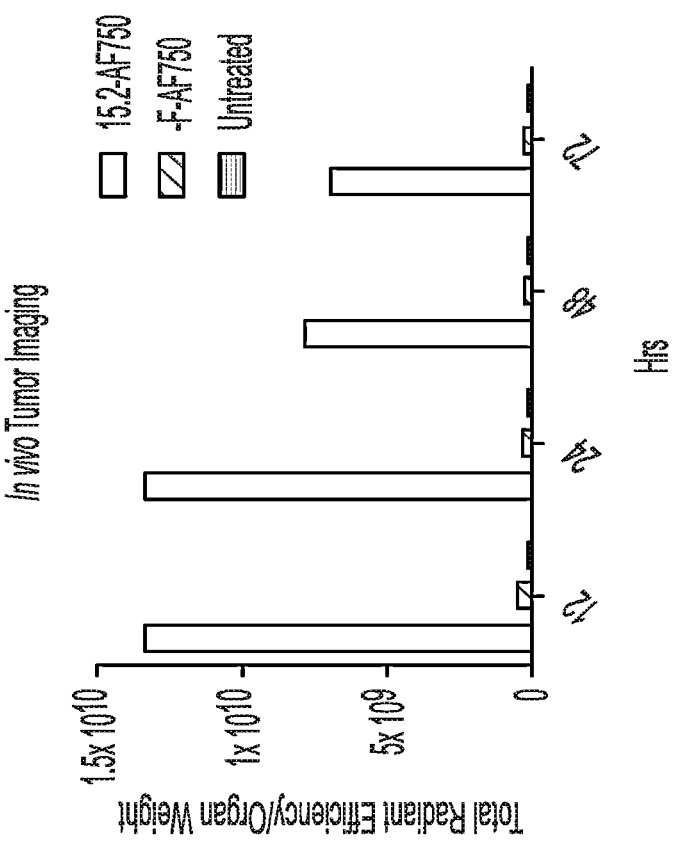
FIG. 18

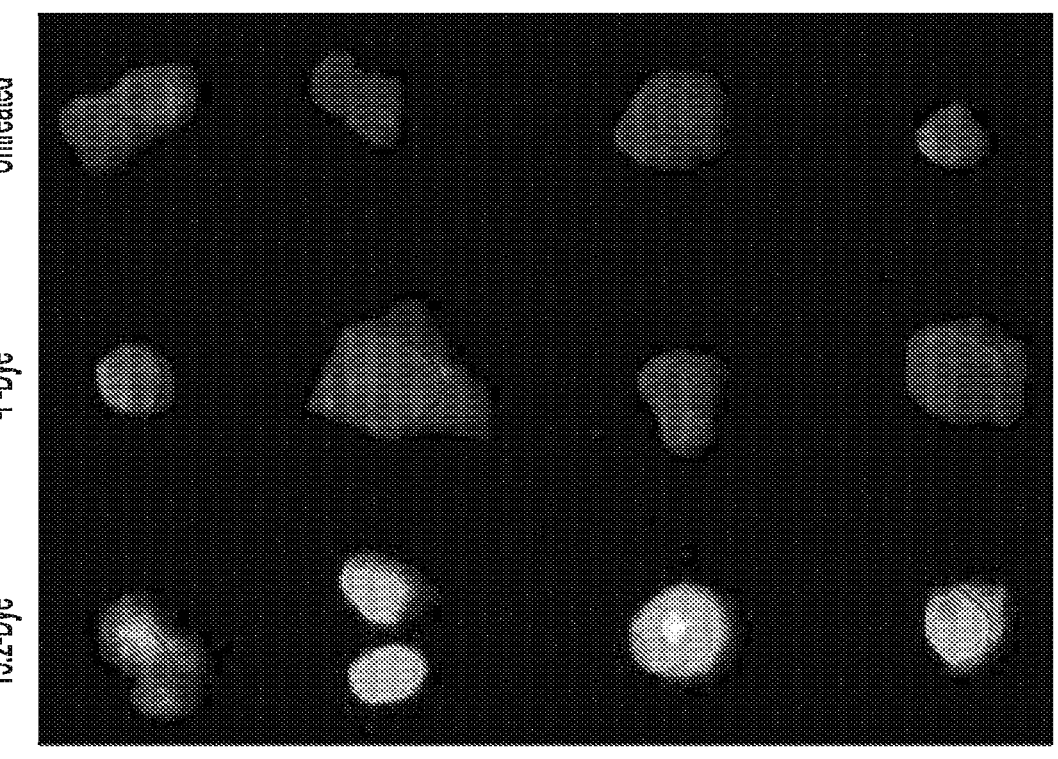
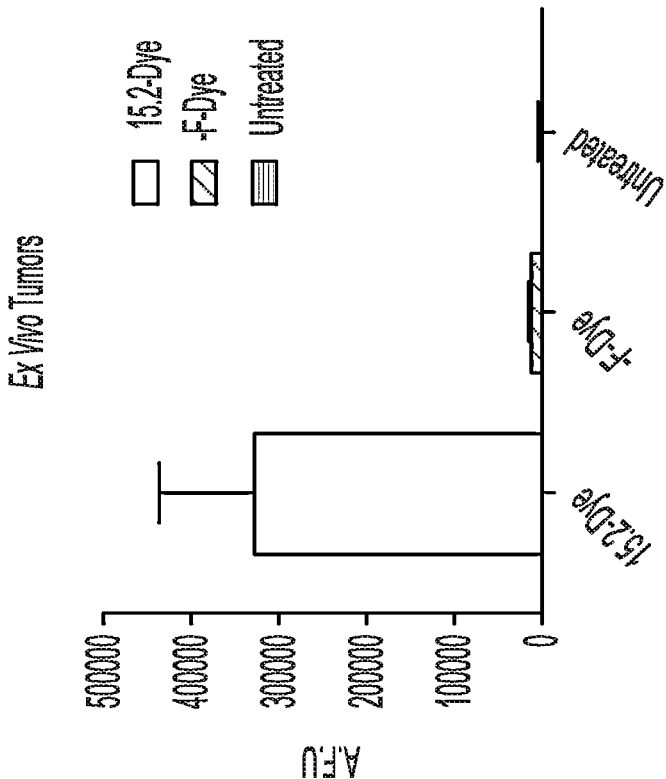
FIG. 19

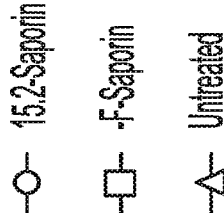
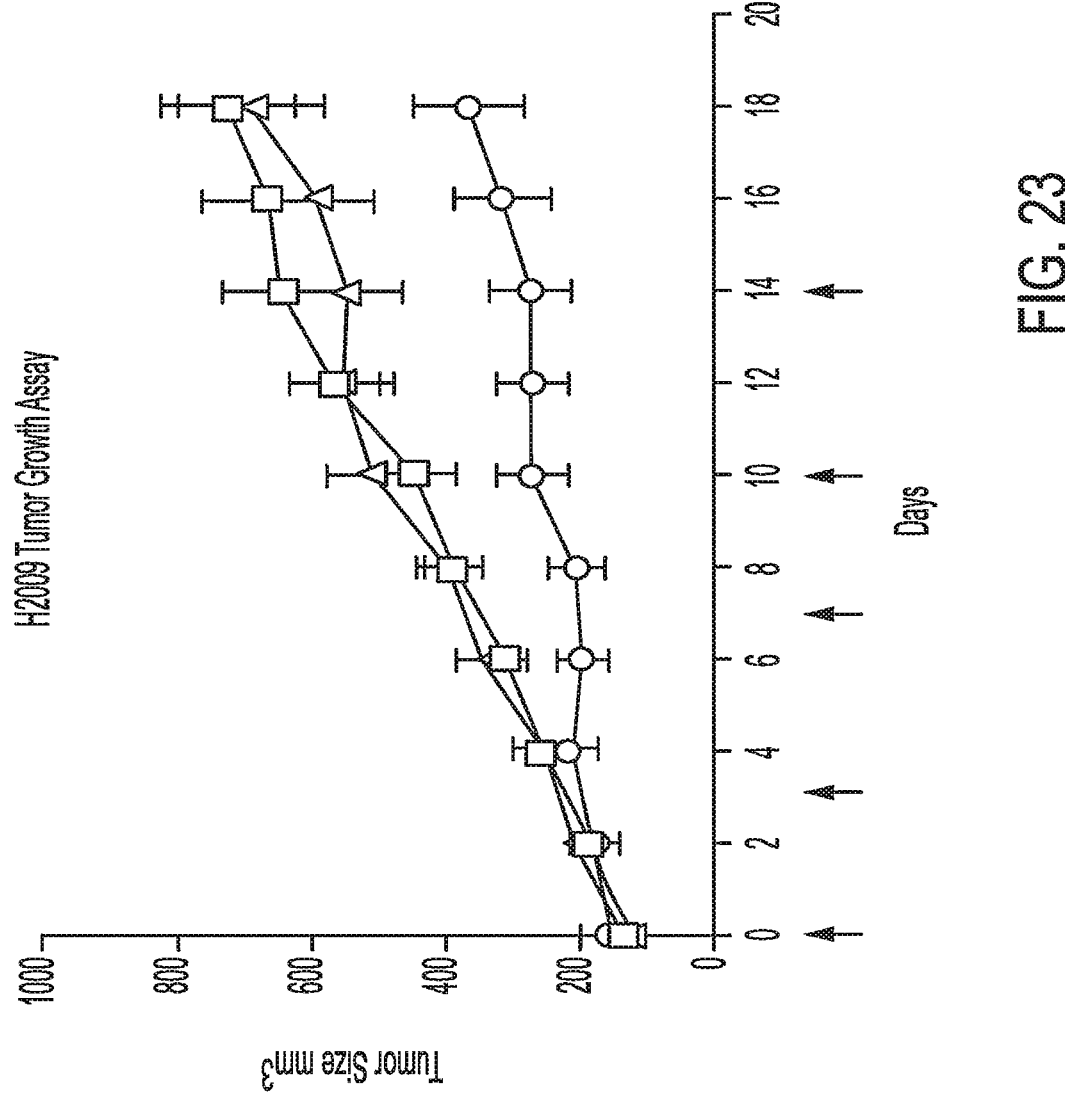
FIG. 23

| Indication | Cell Type Targeted | MGSs identified | |
|---|---|---|---|
| | | MSG Code and Cellular Location | Payloads Delivered |
| Carcinomas and Solid Tumors | Human Non-Small Cell Lung Cancer Cells | MGS_H1299.1_Intracellular<br>MGS_H1299.2_Intracellular<br>MGS_H1299.3_Autophagosomes<br>MGS_H2009.1_Golgi<br>MGS_H2009.2_Lysosome<br>MGS_H2009.3_Lysosome<br>MGS_H2009.4_Golgi/ER<br>MGS_H2009.5_ER/Lysosome<br>MGS_H1993.1_Lysosome<br>MGS_H1993.2_Intracellular<br>MGS_H1993.3_Intracellular<br>MGS_H1993.4_Pre-mitotic cells only<br>MGS_H1993.5_Intracellular<br>MGS_H1993.6_Intracellular<br>MGS_H460.1_PlasmaMembrane<br>MGS_HCC15.1_Intracellular<br>MGS_HCC15.2_Lysosomal<br>MGS_A549.1_Intracellular<br>MGS_HCC95.1<br>MGS_H1155.1<br>MGS_H1155.2<br>MGS_H666.1 | • Monoclonal Antibodies<br>• Small molecule therapeutics (doxorubicin, paclitaxel, DM1, amanitin, auristatin and duocarmycin)<br><br>• Fluorophores<br>• Nanoparticles (liposomes, micelles, quantum dots, SPIO)<br><br>• Imaging agents (PET, NIR, MR)<br>• Peptide and proteins<br>• Proteinaceous toxins<br>• Antigenic peptides<br>• Bead-based capture |

FIG. 24

| | | |
|---|---|---|
| Lymphoma and Leukemia | Lymphoma Cells | MGS_A20.1_Plasma Membrane<br>MGS_A20.2_Plasma Membrane<br>MGS_PCM.1_Plasma Membrane | • Proteins<br>• Fluorophores<br>• Bead-based capture |
| Vaccine Development | Dendritic Cells | MGS_XS52.1_Intracellular<br>MGS_XS52.3_Intracellular | • Liposomes<br>• DNA<br>• Protein antigens<br>• Fluorophores |
| Diabetes | β-Cells of the Islets of Langerhans | MGS_RII.1<br>MGS_RII.2 | • Proteins<br>• Radionuclides |
| Pathogen Infected Cells | Mycoplasma Arginine Infected Cells | MGS_MArg.1_Bacterial | • Fluorescent dyes<br>• Bead-based capture |
| Cardiovascular Disease | Cardiomyocytes | MGS_PCM.1_Intracellular | • DNA<br>• Fluorophores |

1. Intracellular indicates that cellular uptake has been confirmed but the exact intracellular compartment has not been determined.
2. MGS with no location information indicated that cellular binding has been confirmed but cellular location not determined.
3. Peptides highlighted in blue have been shown to home to their target cell in an animal model.
4. The peptides that target NSCLC also bind to cancers derived from other organ sites such as pancreatic, colorectal, breast, and ovarian cancers.

FIG. 24
CONTINUED

| Peptide Code | Cellular Location | New Targeting Peptides (MGS) Isolated at SRI Sequence | Valency | Cancer Specificity |
|---|---|---|---|---|
| H1289.4 | Lysosome | EHPWFNMWSWATQVQEKKK | Tetramer | 10-Fold |
| H2009.2 | Lysosome | YPGSPTQYPSSMHEYHSSSE | Tetramer | In Progress |
| H2009.3 | Golgi/ER | AHTIDDEWASYHMQQWNSPP | Tetramer | In Progress |
| H2009.4 | ER/Lysosome | NLADTWTQTQQHDFHVLRGT | Tetramer | Progress |
| H1993.1 | Lysosome | SVEYWGERMYYDVMESLGFS | Tetramer | 30-Fold |
| H1993.2 | Intracellular | FAAKRAEWMDPGQLWDAVWN | Tetramer | 70-Fold |
| H1993.3 | Intracellular | QEALEEWFWKMMPWSGPSGQ | Tetramer | 2900-Fold |
| H1993.4 | Pre-mitotic cells | TWTDFGQWPWPFGAEGTRAF | Tetramer | 600-Fold |
| H1993.5 | Intracellular | MDGATWWTQLDPLLVWEGET | Tetramer | 20-Fold |
| H1993.5 | Intracellular | SADWFQGPAEWLLEGWMGPL | Tetramer | 30-Fold |

FIG. 25

Human Cell Lines
- HBEC: Nontransformed, immortalized bronchial epithelial cells ("Normal" Control)
- BEAS-2B: Transformed normal human bronchial epithelial cells ("Normal" Control)
- H2009: Human lung adenocarcinoma cell line
- H1993: Human lung adenocarcinoma cell line
- H1299: Human lung large cell carcinoma cell line Binding Profile of New Targeting Peptides at SRI

| | Starting Sequence | Current Sequence | Valency | Half-Maximal Binding for target cell | Serum Stability | bCancer Specificity | Subcellular Location | Validated in Vivo |
|---|---|---|---|---|---|---|---|---|
| aH2009.1 | RGDLATLRQLAQED GVGVR | Ac-D-Leu-RGDLATLRQL | dimer | 17 nM | >99% intact at 12H | | Golgi | Yes |
| H1299.2 | YAAWPASGAWTGT APCSAGT | Ac-YAAWPASGAWT | dimer | 34 nM | | | Internalized | |
| cH1299.3 | LQWRRDDNVHNFG VWARYRL | Ac-LQWRRNFGVWARYRL | dimer | | | >250 fold | autophagasome | Yes |
| HCC15.1 | ATEPRKQYATPRVF WTDAPG | Ac-KQYATPRVFWT | dimer | 5.6 nM | | | Internalized | |
| HCC15.2 | FHAVPQSFYTAP | Ac-FHAVPQSFYT | monomer | 2.7 nM | | | Lysosome | Yes | a. We should discuss this peptide further b. Relative to normal control cell: HBEC. We know the optimized peptides still show specificity but I don't have the numbers relative to the HBEC cell line. These are in progress c. Related to SRI PCT/US15/66519 filed 12/17/2015

FIG. 26

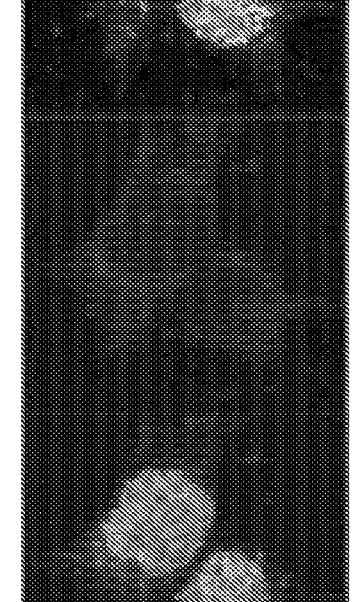
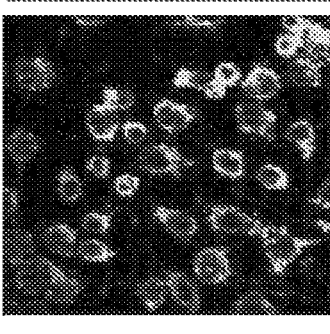
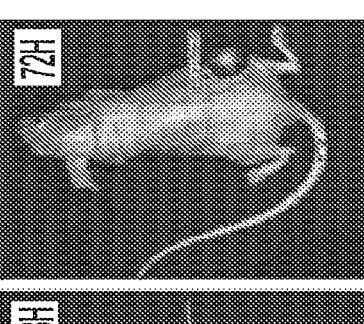
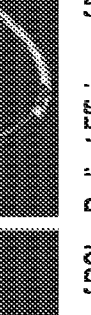
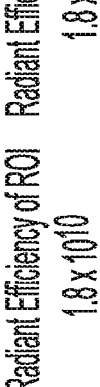
FIG. 27

FIG. 30

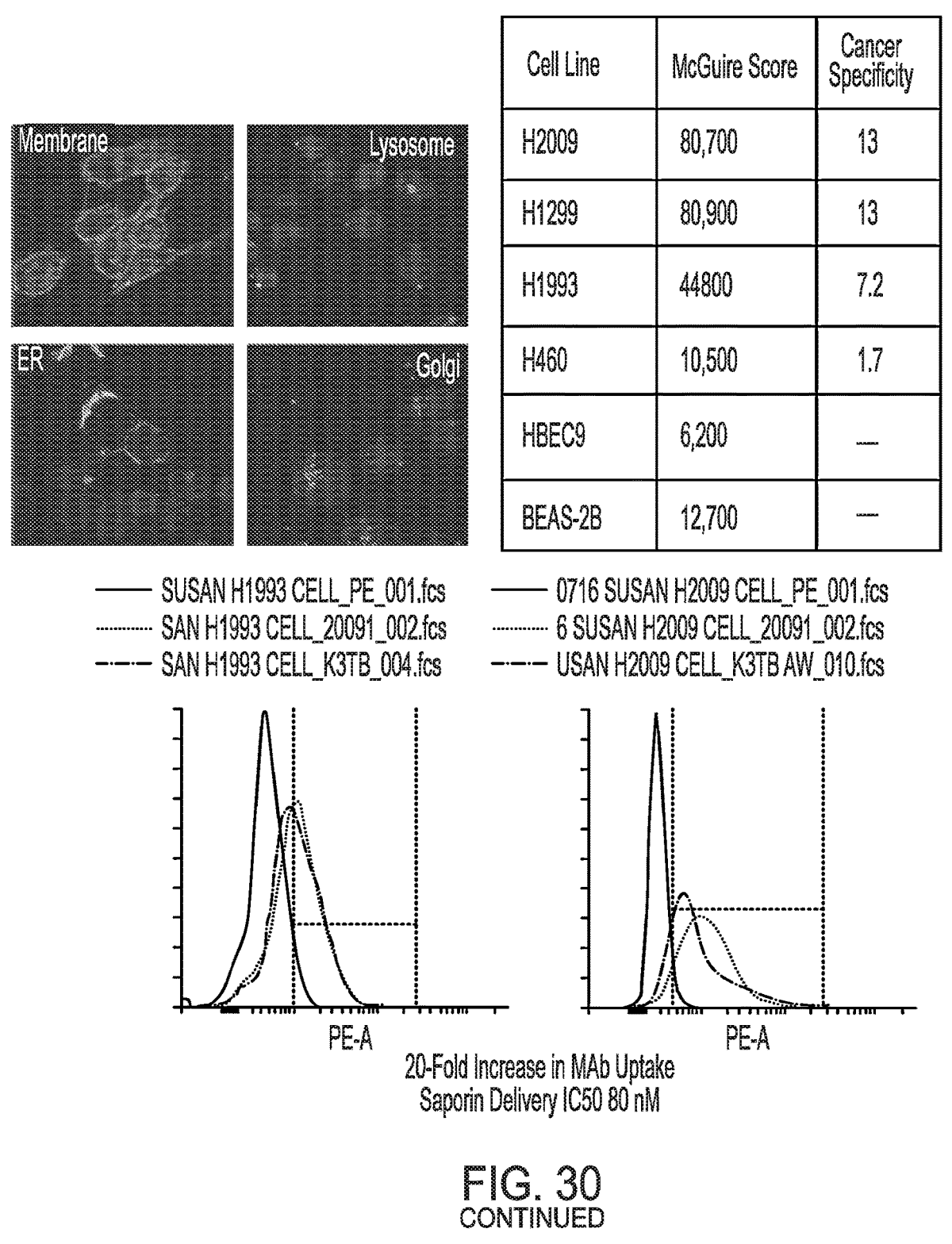

| Cell Line | McGuire Score | Cancer Specificity |
|-----------|---------------|--------------------|
| H2009 | 80,700 | 13 |
| H1299 | 80,900 | 13 |
| H1993 | 44800 | 7.2 |
| H460 | 10,500 | 1.7 |
| HBEC9 | 6,200 | — |
| BEAS-2B | 12,700 | — |

—— SUSAN H1993 CELL_PE_001.fcs
·········· SAN H1993 CELL_20091_002.fcs
—·—· SAN H1993 CELL_K3TB_004.fcs —— 0716 SUSAN H2009 CELL_PE_001.fcs
·········· 6 SUSAN H2009 CELL_20091_002.fcs
—·—· USAN H2009 CELL_K3TB AW_010.fcs

PE-A

PE-A

20-Fold Increase in MAb Uptake
Saporin Delivery IC50 80 nM

FIG. 30
CONTINUED

PEPTIDE SAPORIN CONJUGATE FOR THE TREATMENT OF CANCER

RELATED APPLICATIONS

This application is a continuation of U.S. application Ser. No. 16/629,803, filed Jan. 9, 2020, issued as U.S. Pat. No. 11,738,089 on Aug. 29, 2023, which a U.S. National Stage entry of PCT Application No. PCT/US18/41412, filed Jul. 10, 2018, which further claims benefit of priority from U.S. Provisional Application No. 62/530,674, filed on Jul. 10, 2017, all of which are incorporated herein by reference in their entireties.

STATEMENT REGARDING FEDERALLY FUNDED RESEARCH

This invention was made with government support under Award Number, 7R01CA164447-04 awarded by the Department of Health and Human Services of the National Cancer Institute. The government has certain rights in the invention.

INCORPORATION OF THE SEQUENCE LISTING

The present application contains a sequence listing that was submitted electronically (S1647180103_SequenceListing.xml; Size: 14.427 bytes; and Date of Creation: Feb. 11, 2025), and is herein incorporated by reference in its entirety pursuant to 37 C.F.R. § 1.52(e)(5).

BACKGROUND

American Cancer Society estimates that more than 1.6 million new cancer cases will be diagnosed in the Unites States this year with almost 600,000 deaths due to cancer. The costs to society are immense. The NIH estimates that cancer costs $216.6 billion yearly, of which $89 billion is direct medical costs. First line treatment for most cancers still relies on cytotoxic therapies. These therapies require actively dividing cells resulting in untoward side effects. Treatments are typically given at the maximum tolerated dose not the maximum effective dose. Additionally, these treatments are ineffective in quiescent cancer cells, stems cells or poorly differentiated cancer cells because they are not actively dividing. This leads to reoccurrence. Most targeted therapies that are more specific for tumor biomarkers are cytostatic not cytotoxic. Hence, they may slow the growth of the tumor but not cure it. Finally, resistance to both targeted and untargeted therapies is a clinical reality. Thus, new specific cytotoxic therapies with minimal side effects are needed.

SUMMARY

Saporin is a ribosome inactivating protein (RIP, 34 KD) with no cell entry domain. Given an entry mechanism into the cell, it catalytically removes a single adenine from ribosomal RNA of the large subunit of the ribosome, completely inactivating it. As such, if it can be delivered inside the cell, it is a potent toxin that rapidly kills the cell. Described herein are targeted cancer therapies comprising one or more MGS peptides and the plant toxin saporin. The compositions described herein can, in some aspects, bind to and mediate internalization of the compositions into cancer cells resulting in rapid cell death. Because of the cancer specificity of the MGS peptides, the treatment has minimal effect on normal tissues.

The compositions described herein can be created as a fusion protein or by chemical conjugation. The conjugate can be delivered and the MGS directs the saporin to the tumor and mediates its uptake in the tumor cells where it can bind its target. This compound has several advantages over current therapies. For example, in some aspects, the disclosed compositions (1) can allow for a highly potent cytotoxic to be delivered intracellularly where it is functional; (2) the MGS can be cancer specific minimizing uptake of the toxin in other tissues; (3) because all cells, even non dividing cells, are dependent on protein synthesis, the MGS peptide-saporin conjugate can be effective against cells that are refractory to common cytotoxic agents; (4) resistance is unlikely due to the mechanism of action as a protein, multiple drug resistance pumps are unlikely to negate activity; and (5) the peptidic targeting agent is small, relatively inexpensive compare to antibody targeting agents, and can be conjugated to saporin.

Disclosed herein, are compositions comprising one or more a molecular guidance system (MGS) peptides and a cytotoxic agent.

Disclosed herein, are membrane-permeable conjugates for transport across a lipid membrane comprising: one or more a molecular guidance system (MGS) peptides and a cytotoxic agent.

Disclosed herein, are methods of targeting an intracellular target, the method comprising administering one or more MGS peptides conjugated to a cytotoxic agent, wherein the cytotoxic agent targets an intracellular target.

Other features and advantages of the present compositions and methods are illustrated in the description below, the drawings, and the claims.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 10 shows that the HCC15.2-saporin conjugate reduces tumor growth in a human NSCLC xenograft model.

FIG. 18 shows that HCC 15.2-targeted dye is retained in the tumor over time.

FIG. 19 demonstrates that ex vivo tumors show clear accumulation in HCC 15.2-targeted dye.

FIG. 23 shows that HCC15.2 targeting of saporin markedly slowed tumor growth.

FIG. 24 is a table listing various MGSs, indication, cell type targets, cellular location and payloads delivered.

FIG. 26 is a table showing further characterization of select MGS peptides. Starting sequence from top to bottom: SEQ ID NOs: 7, 5, 36, 32, and 1. Current sequence from top to bottom: SEQ ID NOs: 81, 82, 83, 84 and 80.

FIG. 27 shows co-localization of H1299.3 15-mer with autophagosomes (top panel) and results after administration in vivo.

Figure 30:
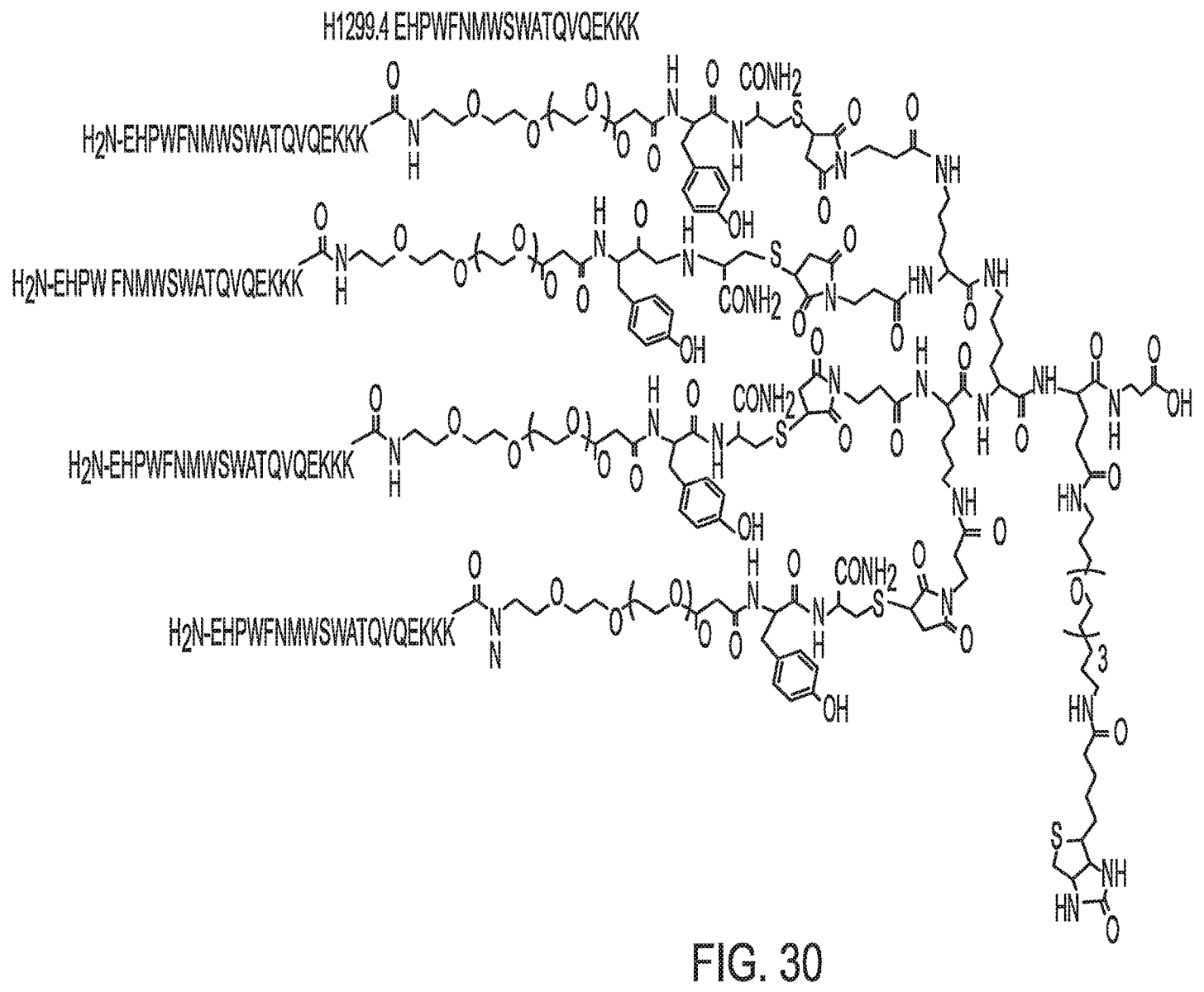

FIG. 30 is an example of a multimeric MGS peptide and experimental results using the multimeric MGS peptide (SEQ ID NO: 22).

DETAILED DESCRIPTION

Figure 1:
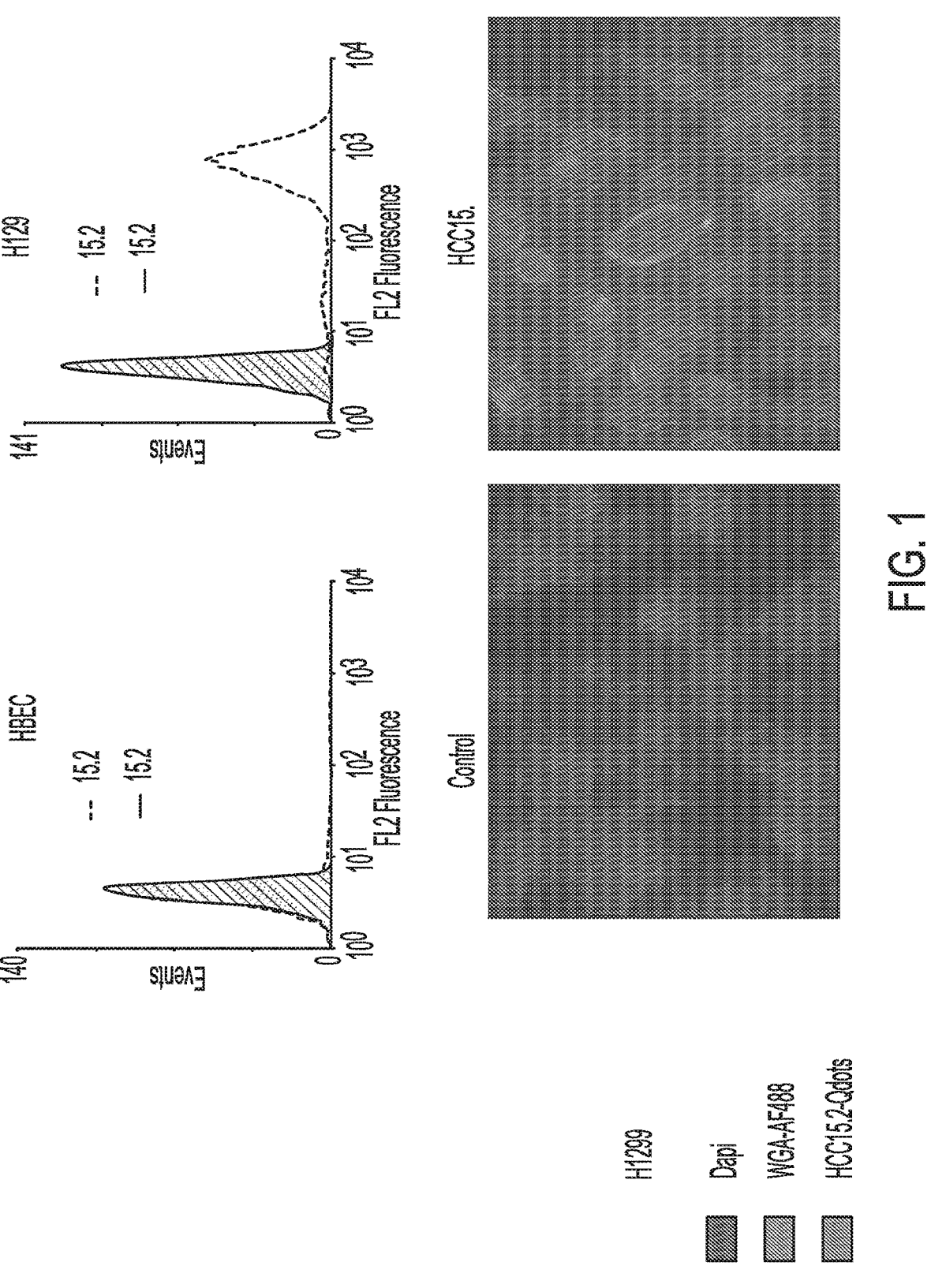
FIG. 1 shows that HCC15.2 is specific for and internalizes in cancer cells.

The disclosed method and compositions may be understood more readily by reference to the following detailed description of particular embodiments and the Examples included therein and to the Figures and their previous and following description.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list. Thus, for example, reference to "a MGS peptide" includes a plurality of such MGS peptides, reference to "the MGS peptide" is a reference to one or more MGS peptides and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for an autoimmune disorder, such as, for example, prior to the administering step.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See *Proteins—Structure and Molecular Properties*

6

2nd Ed., T. E. Creighton, W.H. Freeman and Company, New York (1993); *Posttranslational Covalent Modification of Proteins*, B. C. Johnson, Ed., Academic Press, New York, pp. 1-12 (1983)).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "modulate" is meant to mean to alter, by increasing or decreasing.

As used herein, "effective amount" of a compound is meant to mean a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "treat" is meant to mean administer a compound or molecule of the invention to a subject, such as a human or other mammal (for example, an animal model), that has a cancer, in order to prevent or delay a worsening of the effects of the disease or condition, or to partially or fully reverse the effects of the disease.

As used herein, "prevent" is meant to mean minimize the chance that a subject who has an increased susceptibility for developing cancer will develop cancer.

As used herein, "specifically binds" is meant that an antibody recognizes and physically interacts with its cognate antigen or target (for example, the disclosed synthetic MGS sequences) and does not significantly recognize and interact with other antigens or targets; such an antibody may be a polyclonal antibody or a monoclonal antibody, which are generated by techniques that are well known in the art.

As used herein, "probe," "primer," or "oligonucleotide" is meant to mean a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acids capable of encoding the disclosed MGS sequences (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid capable of encoding the disclosed MGS sequences to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

As used herein, "specifically hybridizes" is meant to mean that a probe, primer, or oligonucleotide recognizes and physically interacts (that is, base-pairs) with a substantially complementary nucleic acid (for example, a nucleic acid capable of encoding the disclosed MGS sequence) under high stringency conditions, and does not substantially base pair with other nucleic acids.

As used herein, "high stringency conditions" is meant to mean conditions that allow hybridization comparable with that resulting from the use of a DNA probe of at least 40 nucleotides in length, in a buffer containing 0.5 M NaHPO$_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, NY, 1998).

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Also disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein.

Disclosed herein is a targeted cancer therapy comprising a peptide conjugate comprising the peptide sequence FHAVPQSFYT (SEQ ID NO: 3) conjugated to the plant toxin saporin. Saporin is a ribosome inactivating protein (RIP, 34 KD) with no cell entry domain. Given an entry mechanism into the cell, it catalytically removes a single adenine from ribosomal RNA of the large subunit of the ribosome, inactivating it. As such, if it can be delivered inside the cell, it is a potent toxin that rapidly kills the cell. As described herein, this problem can be overcome by conjugating saporin to a peptide that is selective for cancer cells and binds to and mediates internalization of the toxin into cancer cells, thus resulting in rapid cancer cell death. Because of the cancer specificity of the MGS peptide conjugate disclosed herein, the treatment has minimal effect on normal tissues.

Disclosed herein is an anti-cancer therapy with applications in lung, breast, colorectal, ovarian, and pancreatic cancers. The compound, composition, or peptide conjugate disclosed herein represents a targeted cytotoxic therapy that may have wide applicability in the treatment of carcinomas.

The composition or conjugate (e.g., the MGS peptide-saporin conjugate) disclosed herein can be created as a fusion protein or by chemical conjugation. The conjugate can be delivered and the MGS peptide can direct the toxin, (e.g., saporin) to the tumor or cancer cell where it mediates the uptake of the saporin into the tumor cells where the toxin can bind its target.

The delivery of the compositions disclosed herein, for example, when one or more molecular guidance system (MGS) peptides when coupled or conjugated to saporin can target and deliver saparoin specifically to cancer cells while avoiding or minimizing the uptake of saporin in normal cells. The MGS peptides disclosed herein have a low nanomolar affinity for a subset of epithelial-derived cancers. Because these MGS peptides are small, they can be easily conjugated to saporin or expressed as a fusion protein. With about 1.6 million new diagnoses and almost 600,000 deaths per year in the U.S. resulting in annual health care costs of approximately $89 billion, the conjugates disclosed herein provide a new therapy for carcinoma that may overcome the limitations of current cancer therapies.

The peptide HCC15.2 can be truncated by removing removal of—one or more amino acids. Further a PEG linker can be added to the monomeric peptide, and the amino terminus can be acetylated.

Compositions

Figure 25:
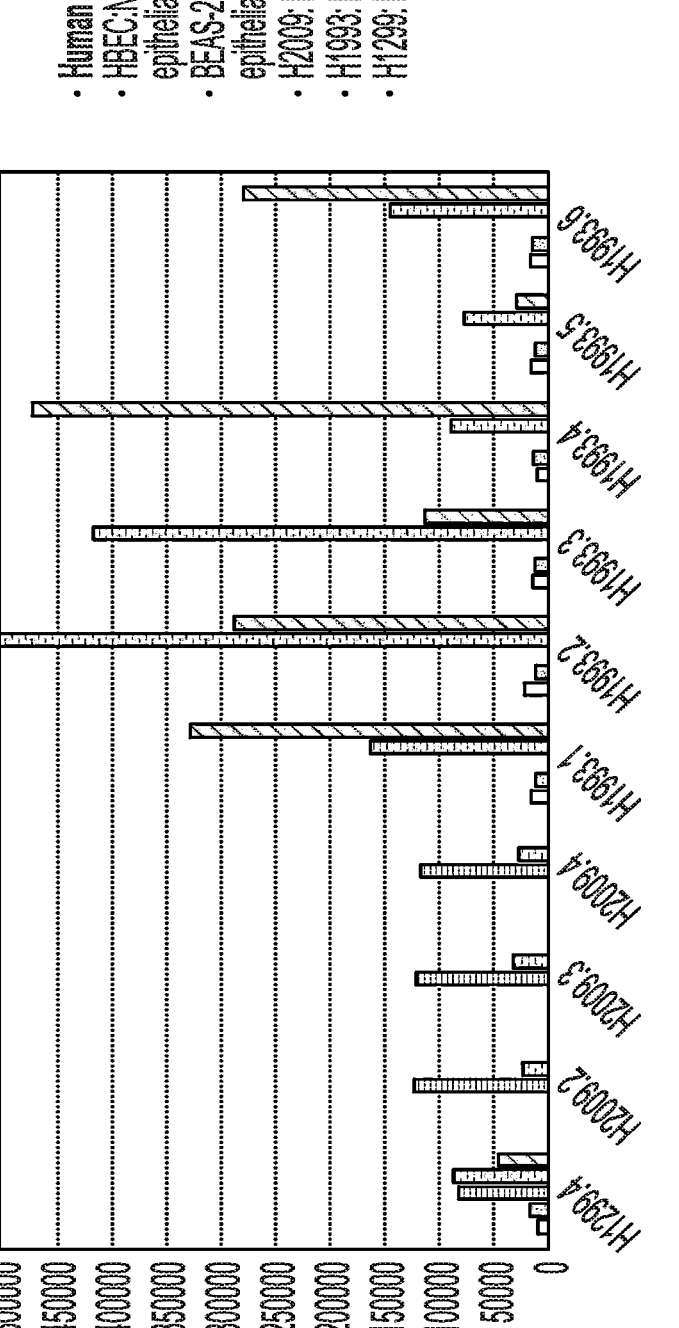
FIG. 25 shows sequences (in order from top to bottom: SEQ ID NOs: 22, 39, 40, 23, 47, 25, 26, 27, 28, and 29) cellular location, valency, cancer specificity and binding profile information for select MGS peptides.

MGS peptides. Disclosed herein are molecular system guidance peptides (MGS) or tumor targeting peptides. These peptides can bind selectively to tumors including malignant tumors. Examples of MGS peptides that can be used or modified in the disclosed compositions can include, but are not limited to, one or more of the MGS peptides disclosed in McGuire et al., Sci Rep. 2014 Mar. 27; 4:4480. Examples of MGS peptides that can also be used in the disclosed compositions and methods, include, but are not limited to the MGS sequences shown in Table 1 and FIGS. 24 and 25.

TABLE 1

Peptide sequences.

| Peptide Name | Peptide Sequence | SEQ ID NO: |
|---|---|---|
| HCC15.2 | FHAVPQSFYTAP | 1 |
| | FHAVPQSFYTA | 2 |
| | FHAVPQSFYT | 3 |
| | FHAVPQSFY | 78 |
| | HAVPQSFYT | 79 |
| | CH$_3$CO-FHAVPQSFYT | 80 |
| H1299.1 | VSQTMRQTAVPLLWFWTGSL | 4 |
| H1299.2 | YAAWPASGAWTGTAPCSAGT | 5 |
| | YAAWPASGAWT | 6 |
| | CH$_3$CO-YAAWPASGAWT | 82 |
| H2009.1 | RGDLATLRQLAQEDGVVGVR | 7 |
| | D-Leu-RGDLATLRQL | 8 |
| | CH$_3$CO-D-Leu-RGDLATLRQL | 81 |
| H460.1 | EAMNSAEQSAAVVQWEKRRI | 9 |
| HCC15.1 | ATEPRKQYATPRVFWTDAPG | 10 |
| A549.1 | MTVCNASQRQAHAQATAVSL | 11 |
| HCC95.1 | MRGQTGKLPTEHFTDTGVAF | 12 |
| H1155.1 | MTGKAAAPHQEDRHANGLEQ | 13 |
| H661.1 | TNSCRGDWLCDAVPEKARV | 14 |
| | EHPWFNMWSWATQVQE | 15 |

TABLE 1-continued

Peptide sequences.

| Peptide Name | Peptide Sequence | SEQ ID NO: |
| --- | --- | --- |
| H2009.2 | YPGSPTQYPSSMHEYHSSSE | 16 |
| H2009.3 | AHTIDDEWASYHMQQWNSPP | 17 |
| | FEEFYSRQSNTIPYPQQYKG | 18 |
| | THGNKHQSWTYPSEINHKNY | 19 |
| | NLADTWTQTQQHDFHVLRGTR | 20 |
| | GYSWWQPNWPSSTWDT | 21 |
| H1299.4 | EHPWFNMWSWATQVQEKKK | 22 |
| H2009.4 | NLADTWTQTQQHDFHVLRGT | 23 |
| H1993.1 | SVEYWGERMYYDVMESLGFS | 24 |
| H1993.2 | FAAKRAEWWDPGQLWDAVWN | 25 |
| H1993.3 | QEALEEWFWKMMPWSGPSGQ | 26 |
| H1993.4 | TWTDFGQWPWPFGAEGTRAF | 27 |
| H1993.5 | MDGATWWTQLDPLLVWEGET | 28 |
| H1993.5 | SADWFQGPAEWLLEGWMGPL | 29 |
| H1299.3 | LQWRRDDNVHNFGVWARYRL | 30 |
| | LQWRRNFGVWARYRL | 31 |
| HCC15.1 | ATEPRKQYATPRVFWTDAPG | 32 |
| | KQYATPRVFWT | 33 |
| | CH$_3$CO-KQYATPRVFWT | 84 |
| MGS_H1299.1 | VSQTMRQTAVPLLWFWTGSL | 34 |
| MGS_1299.2 | YAAWPASGAWTGTAPCSAGT | 35 |
| MGS_1299.3 | LQWRRDDNVHNFGVWARYRL | 36 |
| | CH$_3$CO-LQWRRDDNVHNFGVWARYRL | 83 |
| MGS_H2009.1 | RGDLATLRQLAQEDGVVGVR | 37 |
| MGS_H2009.2 | EHPWFNMWSWATQVQE | 38 |
| MGS_H2009.3 | YPGSPTQYPSSMHEYHSSSE | 39 |
| MGS_H2009.4 | AHTIDDEWASYHMQQWNSPP | 40 |
| MGS_H2009.5 | FEEFYSRQSNTIPYPQQYKG | 41 |
| MGS_HCC15.1 | ATEPRKQYATPRVFWTDAPG | 42 |
| MGS_HCC15.2 | FHAVPQSFYTAP | 43 |
| MGS_H460.1 | EAMNSAEQSAAVVQWEKRRI | 44 |
| MGS_A549.1 | MTVCNASQRQAHAQATAVSL | 45 |
| MGS_MCF7.1 | LTVHGRGPEYNPSWNRRAFP | 46 |
| MGS_H1993.1 | SVEYWGERMYYDVMESLGFS | 47 |
| MGS_H1993.2 | FAAKRAEWWDPGQLWDAVWN | 48 |
| MGS_H1993.3 | QEALEEWFWKMMPWSGPSGQ | 49 |
| MGS_H1993.4 | TWTDFGQWPWPFGAEGTRAF | 50 |

TABLE 1-continued

Peptide sequences.

| Peptide Name | Peptide Sequence | SEQ ID NO: |
|---|---|---|
| MGS_H1993.5 | MDGATWWTQLDPLLVWEGET | 51 |
| MGS_H1993.6 | SADWFQGPAEWLLEGWMGPL | 52 |
| MGS_HCC95.1 | MRGQTGKLPTEHFTDTGVAF | 53 |
| MGS_H1155.1 | MTGKAAAPHQEDRHANGLEQ | 54 |
| MGS_H1155.2 | MEKLPLSKTGRTVSEGVSPP | 55 |
| MGSH666.1 | TNSCRGDWLCDAVPEKARV | 56 |
| MGS_A20.1 | SAKTAVSQRVWLPSHRGGEP | 57 |
| MGS_A20.2 | KSREHVNNSACPSKRITAAL | 58 |
| MGS_PCM.1 | WLSEAGPVVTVRALRGTGSW | 59 |
| MGS_C2C12.1 | TGGETSGIKKAPYASTTRNR | 60 |
| MGS_C2C12.2 | SHHGVAGVDLGGGADFKSIA | 61 |
| MGS_C2C12.3 | SNSPLGLKDEATQRLVLEQAKWLA | 62 |
| MGS_XS52.1 | GPEDTSRAPENQQKTFHRRW | 63 |
| MGS_XS52.2 | SGETGSNLVGHELDFRPGSPSP | 64 |
| MGS_XS106.1 | RYSPAATAEGRSVSKELLRV | 65 |
| MGS_717US.1 | GQELGAWTRSKGPEVQTSVL | 66 |
| MGS_717S.1 | ASTWRGTSAGGNRLEKMEVT | 67 |
| MGS_RIP.1 | LSGTPERSGQAVKVKLKAIP | 68 |
| MGS_RIP.2 | GAWEAVRDRIAEWGSWGIPS | 69 |
| MGS_MArg.1_Bacterial | AMDMYSIEDRYFGGYAPEVG | 70 |
| MGS_1299.2 V4 | $CH_3CO$-YAAWPASGAWT-$PEG_{11}$-C-$NH_2$ | 71 |
| MGS_1299.3 V2 | $CH_3CO$-LQWRRNFGVWARYRL-$PEG_{11}$-C-$NH_2$ | 72 |
| MGS_2009.1 V4 | $CH_3CO$-RGDLATLRQL-$PEG_{11}$-YC-$NH_2$ | 73 |
| MGS_H2009.1 V5 | $CH_3CO$-d(Leu)-RGDLATLRQL-$PEG_{11}$-YC-$NH_2$ | 74 |
| MGS_HCC15.1 V4 | $CH_3CO$-LQWRRNFGVWARYRL-$PEG_{11}$-C-$NH_2$ | 75 |
| MGS_HCC15.2 V8 | $CH_3CO$-FHAVPQSFYT-$PEG_{11}$-C-$NH_2$ | 76 |
| MGS_HCC15.2 V9 | $CH_3CO$-FHAVPQSFYT-$PEG_{11}$-C-$NH_2$ | 77 |

In an aspect, the compositions comprise one or more a molecular guidance system (MGS) peptides and a cytotoxic agent. In an aspect, the membrane-permeable conjugates for transport across a lipid membrane can comprise one or more a molecular guidance system (MGS) peptides and a cytotoxic agent.

In an aspect, the one or more MGS peptides can be any of the MGS peptides disclosed herein. In an aspect, the one or more MGS peptides comprise SEQ ID NO: 1, 2, 3, 34, 35, 36, 37, 38, 39, 40, 41, 41, 42, 43, 44, 45, 46, 47, 48, 49, 50, 51, 52, 5, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84 or a combination thereof. In an aspect, the one or more MGS peptides comprise SEQ ID NOs: 1, 2 or 3. In an aspect, the cytotoxic agent can be saporin or a biologically active variant thereof. In an aspect, the one or more MGS peptides can be SEQ ID NO: 3 and the cytotoxic agent can be saporin. In an aspect, the compositions can comprise one or more MGS peptides, for example, in some aspects, the composition can comprise, one, two, three, four or five MGS peptides. In an aspect, the one or more MGS peptides can form a tetrameric scaffold protein. In an aspect, the one or more MGS peptides disclosed herein can be truncated. In an aspect, the one or more MGS peptides can be modified. In an aspect, the one or more MGS peptides can acetylated on the N-terminus. FIG. 26 provides examples of select MGS peptides that have been further characterized. In an aspect, the one or more MGS peptides can be chemically conjugated to the cytotoxic agent. In an aspect, the chemical conjugate can be polyethylene glycol (PEG). In an aspect, the number of PEG units can be 1, 2, 3, 4, 5, 6, 7, 8, 9, 10, 11, or more. In aspect, the number of PEG units can be of sufficient length to separate the one or more MGS peptides from the cytotoxic agent to prevent any steric interference between the one or more MGS peptides and the cytotoxic agent. For example, disclosed herein are compositions comprising a chemical conjugate, wherein the chemical conjugate is PEG and the PEG comprises eleven PEG units. In an aspect, the one or more MGS peptides comprise SEQ ID NO: 3, wherein SEQ ID NO: 3 can be acetylated on the N-terminus and can be chemically conjugated to PEG; and the cytotoxic agent can be saporin, wherein the saporin can be covalently attached to PEG.

Cytotoxic Agents. A wide variety of toxic (e.g., cytotoxic) agents can be included in the disclosed compositions. The cytotoxic agents can be covalently conjugated or form a fusion protein with one or more of the MGS peptides disclosed herein. The cytotoxic agent can be a protein. In an aspect, the cytotoxic agent can be a bacteria or plant toxin. In some aspects, the cytotoxic agent can be a plant toxin. In an aspect, the cytotoxic agent can be saporin or a biological variant thereof. The cytotoxic agent can be modified. In an aspect, the cytotoxic agent is a fragment of a bacterial or plant toxin.

The methods of making the conjugates or fusion proteins are known to one of ordinary skill in the art and can be carried out using known techniques. In an aspect, the MGS peptides are conjugated to a cytotoxic agent (e.g., saporin) using polyethylene glycol. It is within the skill of an ordinary person in the art to chemically conjugate the MGS peptides disclosed herein with the optimal PEG units.

Labels. Also described herein are composition comprising one or more molecular guidance system (MGS) peptides and a label. For example, the compositions disclosed herein can include detectable labels. Such detectable labels can include, but are not limited to, a tag sequence designed for detection (e.g., purification or localization) of an expressed polypeptide or sequence. Tag sequences include, for example, green fluorescent protein, glutathione S-transferase, polyhistidine, c-myc, hemagglutinin, or Flag™ tag, and can be fused with an encoded nucleic acid. Such detectable labels can include, but are not limited to, a fluorescent agent, an enzymatic label, or a radioisotope.

Pharmaceutical Compostions

Disclosed herein are pharmaceutical compositions comprising one or more of the compositions disclosed herein and a pharmaceutical acceptable carrier described above. In some aspects, the MSG peptide can be SEQ ID NO: 3 and the cytotoxic agent can be a saporin or a biological variant thereof and the pharmaceutical composition is formulated for intravenous administration. The compositions of the present disclosure also contain a therapeutically effective amount of the cytotoxic agent as described herein. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the fusion proteins. Thus, compositions can be prepared for parenteral administration that includes fusion proteins dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein, are methods of treating a subject with cancer, the method comprising: (a) identifying a subject in need of treatment; and (b) administering to the subject a therapeutically effective amount of the pharmaceutical composition comprising one or more a molecular guidance system (MGS) peptides and a cytotoxic agent, and a pharmaceutically acceptable carrier. The MGS peptides can be any of the MGS peptides disclosed herein. The cytotoxic agent can be saporin or a biologically variant thereof.

Disclosed herein are methods of targeting an intracellular target. The method can comprise administering one or more MGS peptides conjugated to a cytotoxic agent. The cytotoxic agent can target an intracellular target. In an aspect, the intracellular target can be a lysosome, golgi apparatus, endoplasmic reticulum, cytoplasm, or nucleus.

In an aspect, skilled person can determine an efficacious dose, an efficacious schedule, or an efficacious route of administration for a disclosed composition or a disclosed fusion protein or a disclosed fusion protein so as to induce target an intracellular target such that the intracellular target can be inactivated.

In an aspect of any of the disclosed methods herein, the composition, conjugate or fusion protein described herein can be combined with one or more additional therapies. In an aspect, the composition, conjugate or fusion protein can be administered alone or in combination with other biologically active agents into compositions suitable for administration to a subject. In an aspect, methods directed to treating subjects with cancer or at risk for developing cancer, the composition, conjugate or fusion protein disclosed herein can be combined with, for example, therapeutically effective amount of radiation therapy, immunotherapy or chemotherapy or a combination thereof. The combined therapy can be administered as a co-formulation, or separately. When administered separately, the combined therapy can be administered simultaneously or sequentially. The formulations can be made using methods routine in the art.

The pharmaceutical compositions described above can be formulated to include a therapeutically effective amount of a composition, conjugate or fusion protein as disclosed herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to one or more autoimmune diseases or where the patient has a clinically determined predisposition or increased susceptibility (in some cases, a greatly increased susceptibility) to cancer.

The pharmaceutical compositions described herein can be administered to the subject (e.g., a human subject or human patient) in an amount sufficient to delay, reduce, or preferably prevent the onset of clinical disease. Accordingly, in some aspects, the subject is a human subject. In therapeutic applications, compositions are administered to a subject (e.g., a human subject) already with or diagnosed with an autoimmune disease in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effective amount includes amounts that provide a treatment in which the onset or progression of the cancer is delayed, hindered, or prevented, or the autoimmune disease or a symptom of the autoimmune disease is ameliorated. One or more of the symptoms can be less severe. Recovery can be accelerated in an individual who has been treated.

In some aspects, the cancer can be a primary, secondary, refractory or relapsing tumor. In an aspect, the cancer can be lung cancer, breast cancer, colorectal cancer, ovarian cancer or pancreatic cancer.

Amounts effective for this use can depend on the severity of the cancer and the weight and general state and health of the subject. Suitable regimes for initial administration and booster administrations are typified by an initial administration followed by repeated doses at one or more hourly, daily, weekly, or monthly intervals by a subsequent administration.

The total effective amount of the conjugates or fusion proteins in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of the toxins (or cytotoxic agents) present within the compositions described herein and used in the methods as disclosed herein applied to mammals (e.g., humans) can be determined by one of ordinary skill in the art with consideration of individual differences in age, weight, and other general conditions (as mentioned above). Because the compositions, conjugates and fusion proteins of the present disclosure can be stable in serum and the bloodstream and in some cases more specific, the dosage of the compositions, conjugates and fusion proteins including any individual component can be lower (or higher) than an effective dose of any of the individual components when unbound. Accordingly, in some aspects, the toxin administered can have an increased efficacy or reduced side effects when administered as part of a conjugate or fusion protein as compared to when the toxin is administered alone or not as part of a conjugate or fusion protein.

Vectors

Disclosed are vectors comprising the nucleic acid sequence that encodes for one or more of the disclosed compositions. In some aspects, the vector comprises only a nucleic acid sequence capable of encoding one or more of the disclosed MGS peptides.

Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits comprising one or more of the disclosed compositions.

In some aspects the kits comprise a MGS peptide and a cytotoxic agent and instructions for conjugation.

In some aspects the kits comprise a cell line comprising the nucleic acid sequence that encodes one or more of the MGS peptides.

Figure 2:
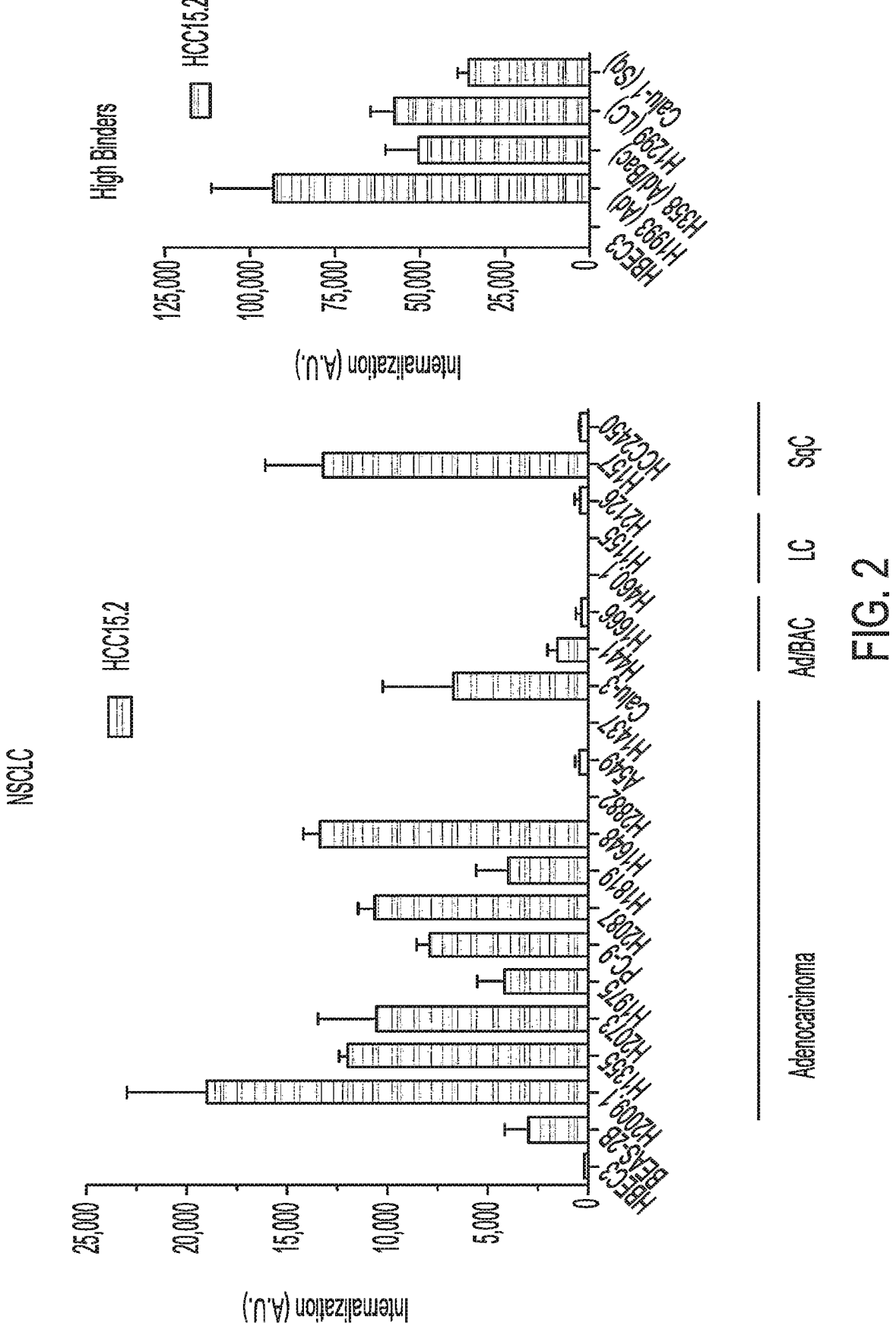
FIG. 2 shows that HCC15.2 binds to all subtypes of NSCLC.

EXAMPLES a. Example 1: HCC15.2 Shows Specificity to and Internalizes in Cancer Cells In order for the peptides to be clinically useful reagents, discriminating between normal and cancer cells can be important. FIG. 1 shows that the MGS peptide, HCC15.2, accumulates in cancer cells and is specific compared to control. HCC15.2 binding was analyzed by flow cytometry analysis (see, FIG. 1). The HCC15.2 does not bind to normal HBEC's but binds to the LC line H1299. The binding was sequence dependent and not specific for a single histopathological class (see, FIG. 2).

MGS peptides were synthesized using standard solid-phase FMOC techniques on a Prelude synthesizer (Protein Technologies Inc.). MGS peptides were purified via reverse phase HPLC on a C18 prep column to >95% purity, and verified by MALDI-TOF. The optimized HCC15.2 Peptide sequence is Ac-FHAVPQSFYT-PEG11-Biotin and has a molecular weight of 2394 Da, and Ac-FHAVPQSFYT-PEG11-C with a molecular weight of 1940 Da. Tetrameric HCC15.2 was synthesized via previously published protocols. Stock solutions were made in PBS pH 7.4 and concentration determined by absorbance at 280 nM on a Nanodrop 2000 (Thermo Fisher Scientific).

Flow Cytometry. Biotinylated peptide was conjugated to streptavidin-R-phycoerythrin (1:1) for 30 min at RT. The remaining binding sites on streptavidin were quenched with RPMI 1640 and solution diluted to 25 nM. Tumor cells were grown to 90% confluency in a 12 well plate, then incubated with 500 μl peptide-dye conjugate for 1 hour at 37 C. After 1 hour, peptide was removed and the cells were washed 3× with PBS for 5 min, 2× with acid rinse, and 1×PBS rinse. Added 300 μl trypsin until cells lifted then added 700 μl RPMI+5% FBS to inactivate the trypsin. Cells were transferred to a flow tube, and put on ice in the dark. Flow cytometry was run on BD FACSCelesta and data were analyzed on Flowing software. A region containing <5% of the cells in the negative control is established and the McGuire score is calculated for each sample by multiplying the % of positive cells by the fluorescence intensity.

Figure 11:
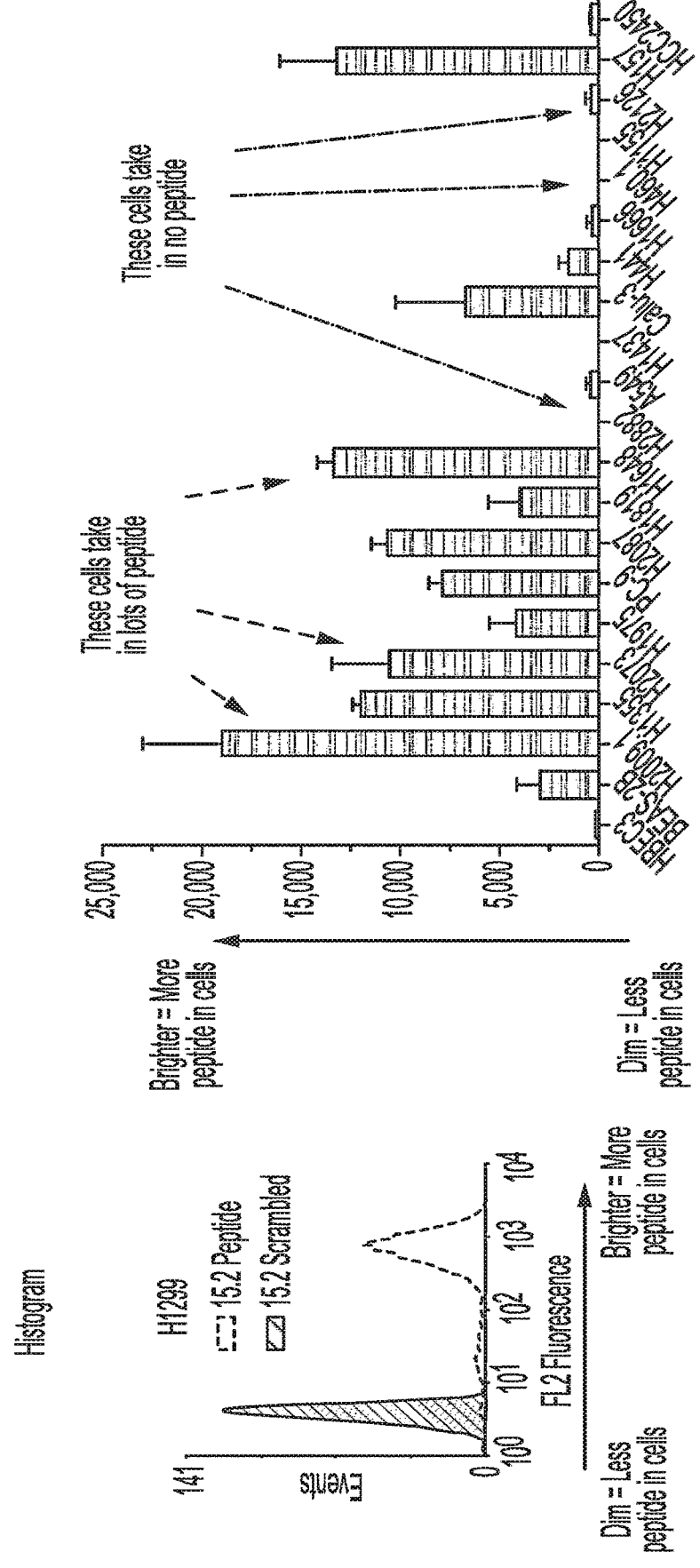
FIG. 11 depicts a histogram and a quantification of a histogram from flow cytometry experiments.

For the flow cytometry experiments, cells are treated with a peptide (e.g., a MGS peptide) that has a dye on it for one hour. If the peptide enters the cell(s), the dye will also enter the cell(s) (see, FIG. 11). Next, the cells are washed and placed in a tube to run flow cytometry. The flow cytometer can measure the brightness of 10,000 or more individual cells.

Confocal Microscopy. Plasmids with organelle specific markers labeled with GFP were purchased from Addgene and electroporated into H1299 cells. After G418 selection, GFP-labeled tumor cells were plated on 8 well chamber slides on the day previous to the study. Biotinylated peptide was conjugated to streptavidin-AlexaFluor 555 (1:1) for 30 min at RT and quenched with RPMI, then added to the wells at 50 nM. After 1 hour incubation cells were washed for 5 min 3× with PBS, 2× acid rinses, and 1×PBS rinse. Cells were fixed in 2% formaldehyde for 10 min, washed with PBS, stained with DAPI in mounting media and coverslip was added. Microscopy was acquired on a Zeiss LSM 700 with a Pln Apo 63×/1.4 oil DIC III objective. Compressed images were obtained using ImageJ software maximal intensity projections.

For the microscopy experiments, cells are treated with a peptide (e.g., a MGS peptide) that has a dye on it for one hour. If the peptide enters the cell(s), the dye will also enter the cell(s) (see, FIG. 1). Next, the cells are washed and fixed to glass plate. Other parts of the cell (e.g., cell membrane, organelles or nucleus) are stained. Fluorescent microscopy is performed to assess the dyes in the cells. Confocal microscopy is used to take a series of sliced images that can be used to build a 3D picture (like an MRI).

b. Example 2: HCC15.2 Internalization is Receptor Mediated

Figure 3:
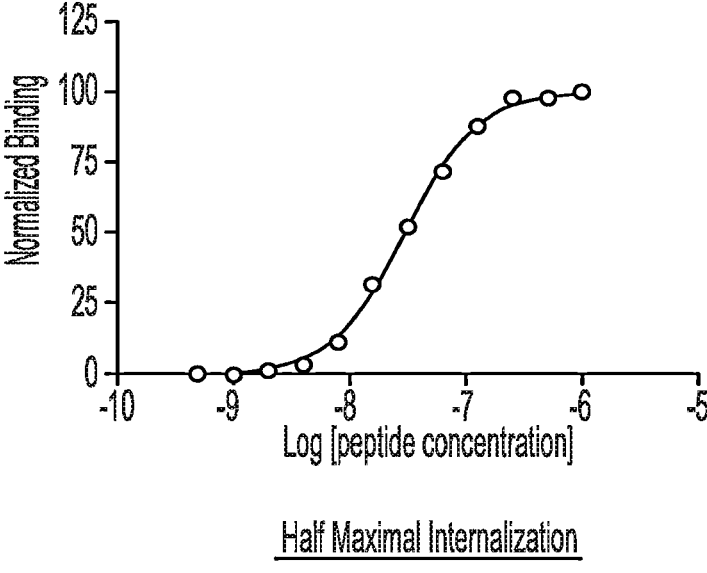
FIG. 3 shows that peptide internalization is receptor mediated.
Figure 12:
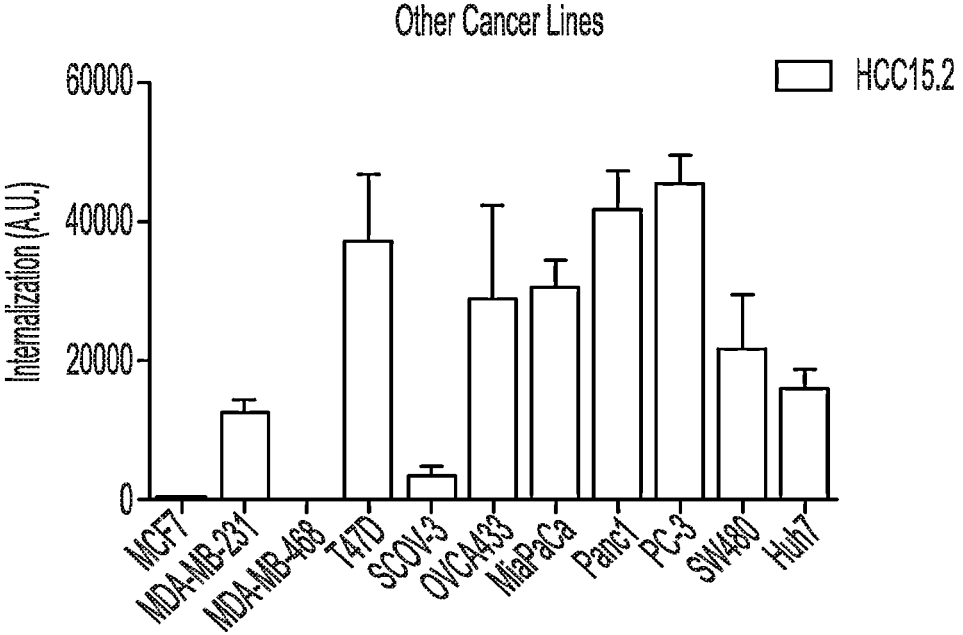
FIG. 12 is a bar graph showing that HCC15.2 binds to other cancer cell lines.

Experiments were carried out that show that HCC15.2 can be internalized and this internalization is receptor mediated (see, FIG. 3). More specifically, HCC15.2 binds to a specific subset of NSCLC and other tumor cells (see, FIG. 12). Phage blocking was used as a control. HCC15.2 was internalized by a specific panel of cell lines and not others. The results also show that the internalization mediated by a receptor was sequence specific. Treating with trypsin 2 min before adding HCC15.2 resulted in no internalization. Also, HCC15.2 does not internalize at 4° C.

Figure 4:
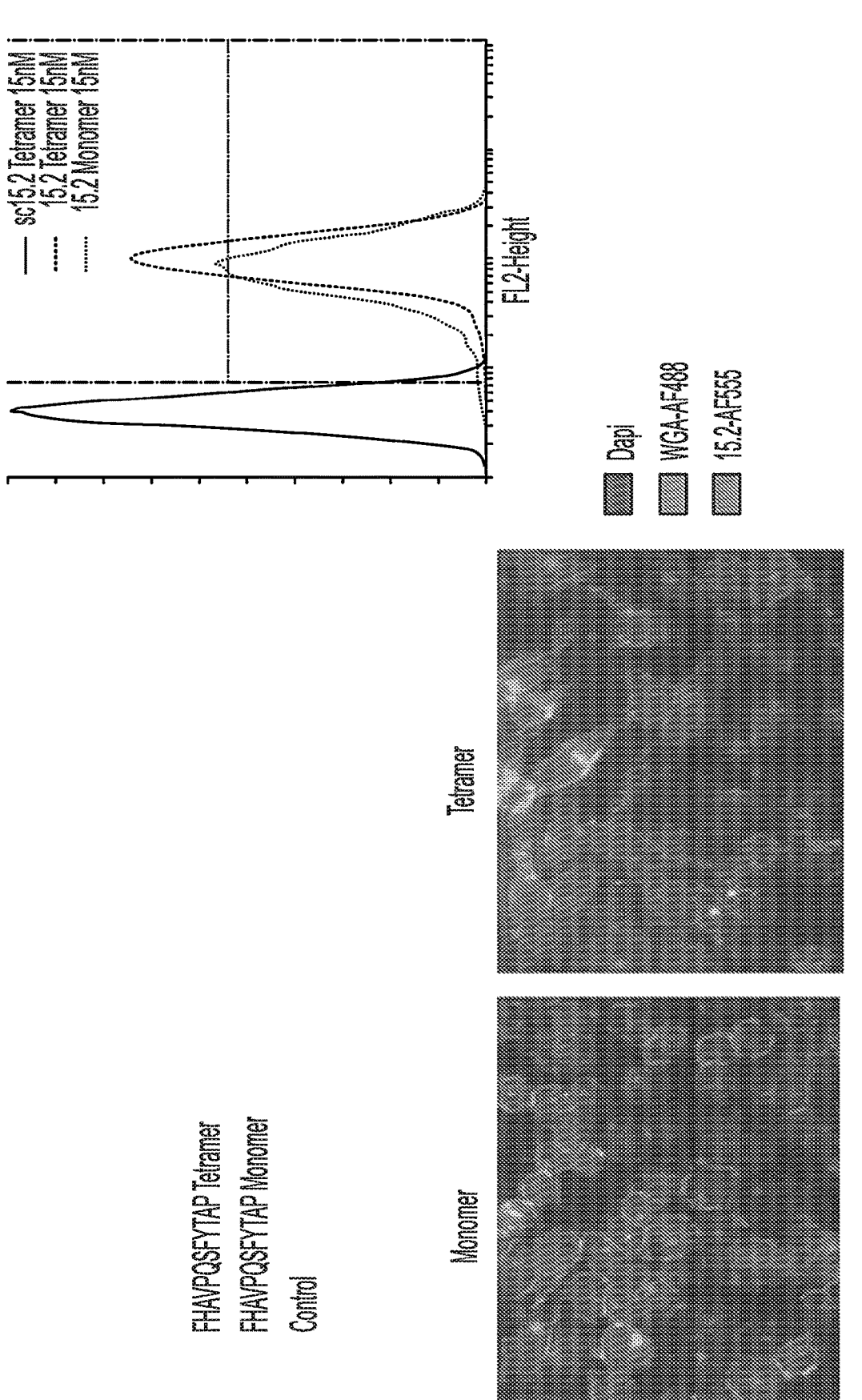
FIG. 4 shows that tetramerization of SEQ ID NO: 1 does not significantly improve internalization compared to the monomer of SEQ ID NO: 1.

FIG. 4 shows that the tetramerization of HCC15.2 does not significantly improve receptor mediated internalization. This result is surprising as most peptides studied and identified through the FOX3 molecular guidance system had non-additive increase in binding/internalization.

c. Example 3: Truncations of HCC15.2

Figure 5:
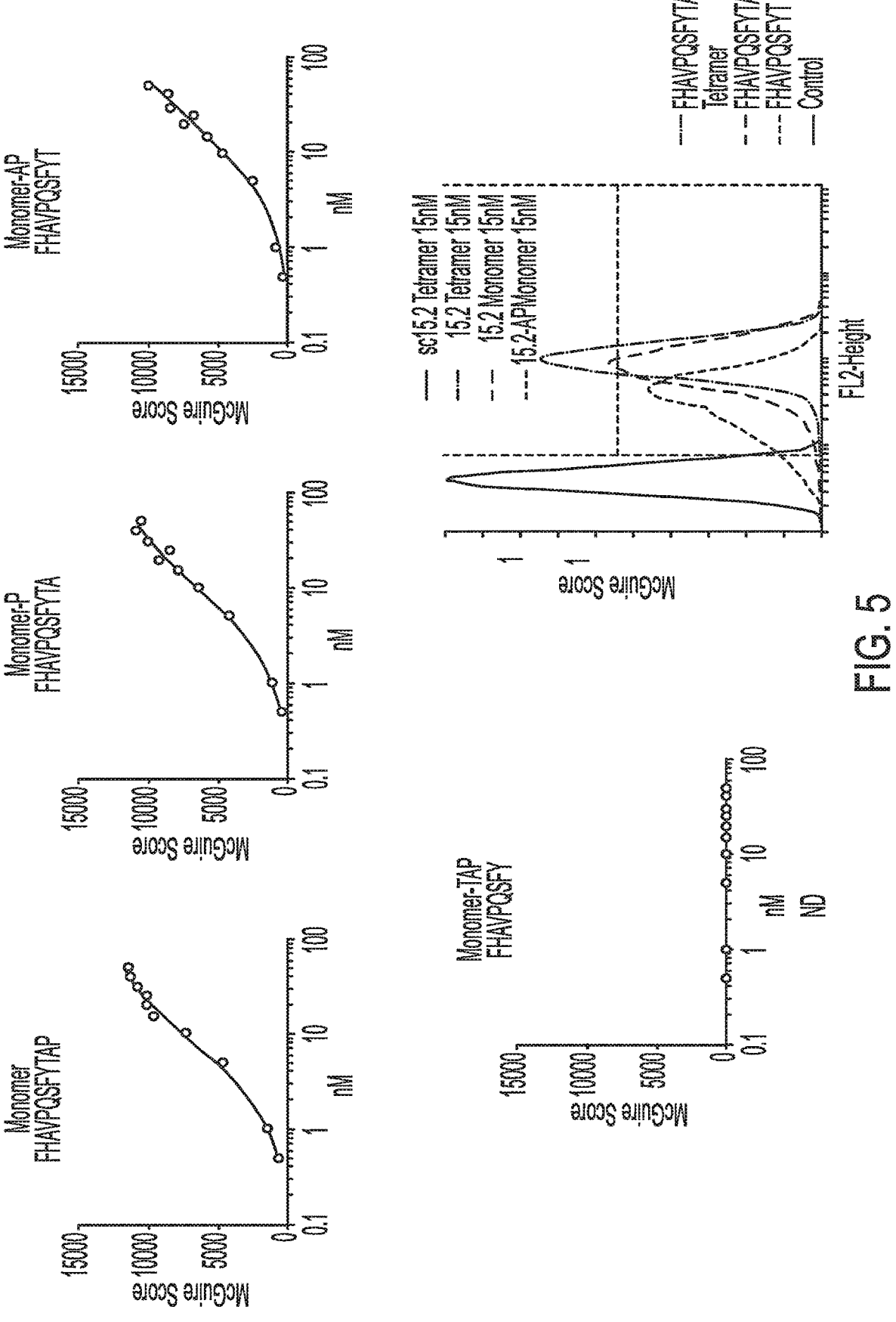
FIG. 5 shows that truncations from N- and C-Terminal ends reveal minimal binding sequence (FHAVPQSFYTAP, SEQ ID NO: 1; FHAVPQSFYTA, SEQ ID NO: 2; and FHAVPQSFYT, SEQ ID NO: 3).
Figure 15:
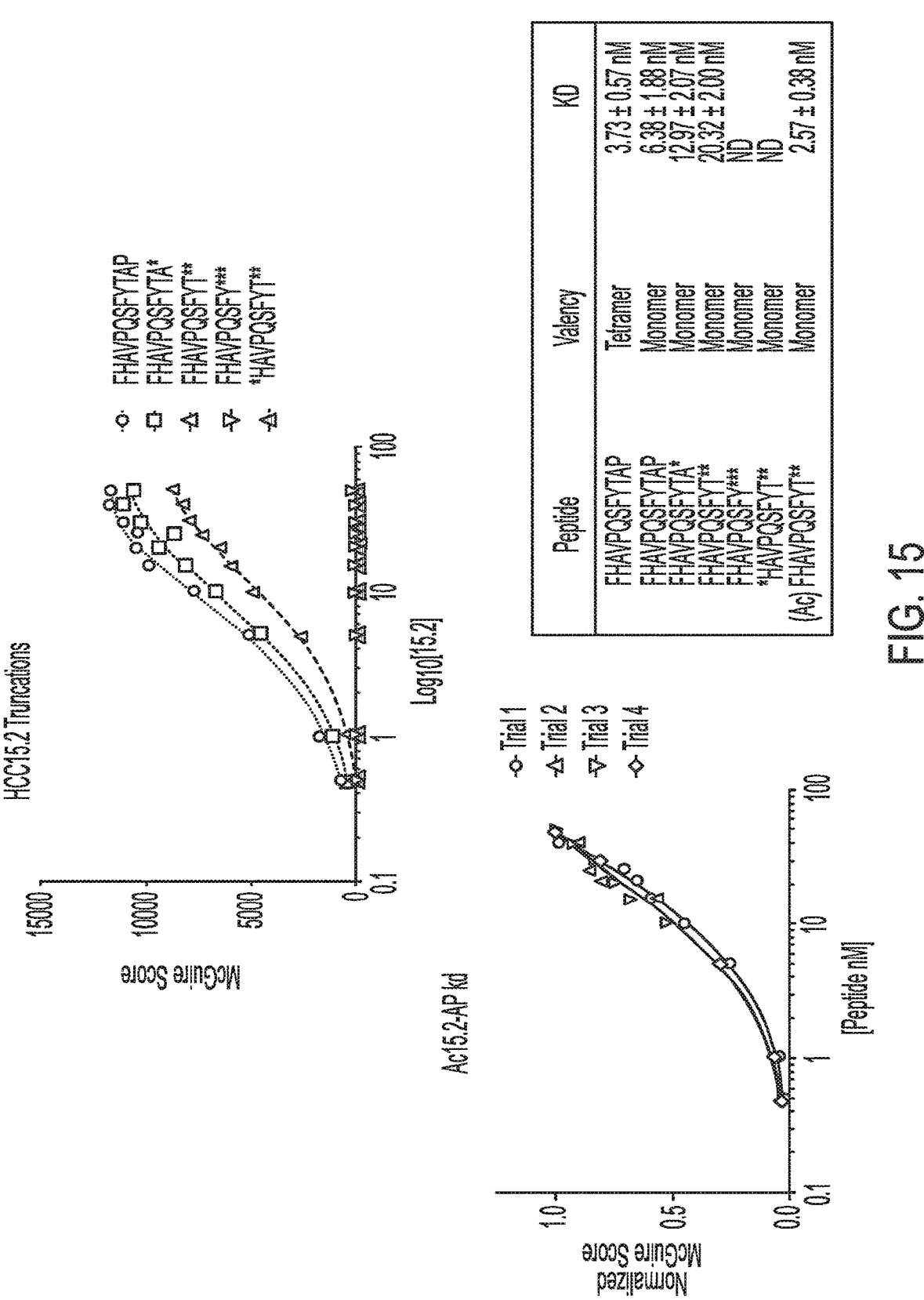
FIG. 15 shows that truncations from N- and C-Termini reveal minimal binding sequence. Top panel refers to the following sequences from top to bottom: SEQ ID NOs: 1, 2, 3, 78, and 79. Bottom panel refers to the following sequences from top to bottom: SEQ ID NOs: 1, 2, 3, 78, 79, and 80.

FIG. 5 and FIG. 15 show that the truncations from N- and C-Terminal ends of the HCC15.2 peptide reveal minimal binding sequence.

Figure 6:
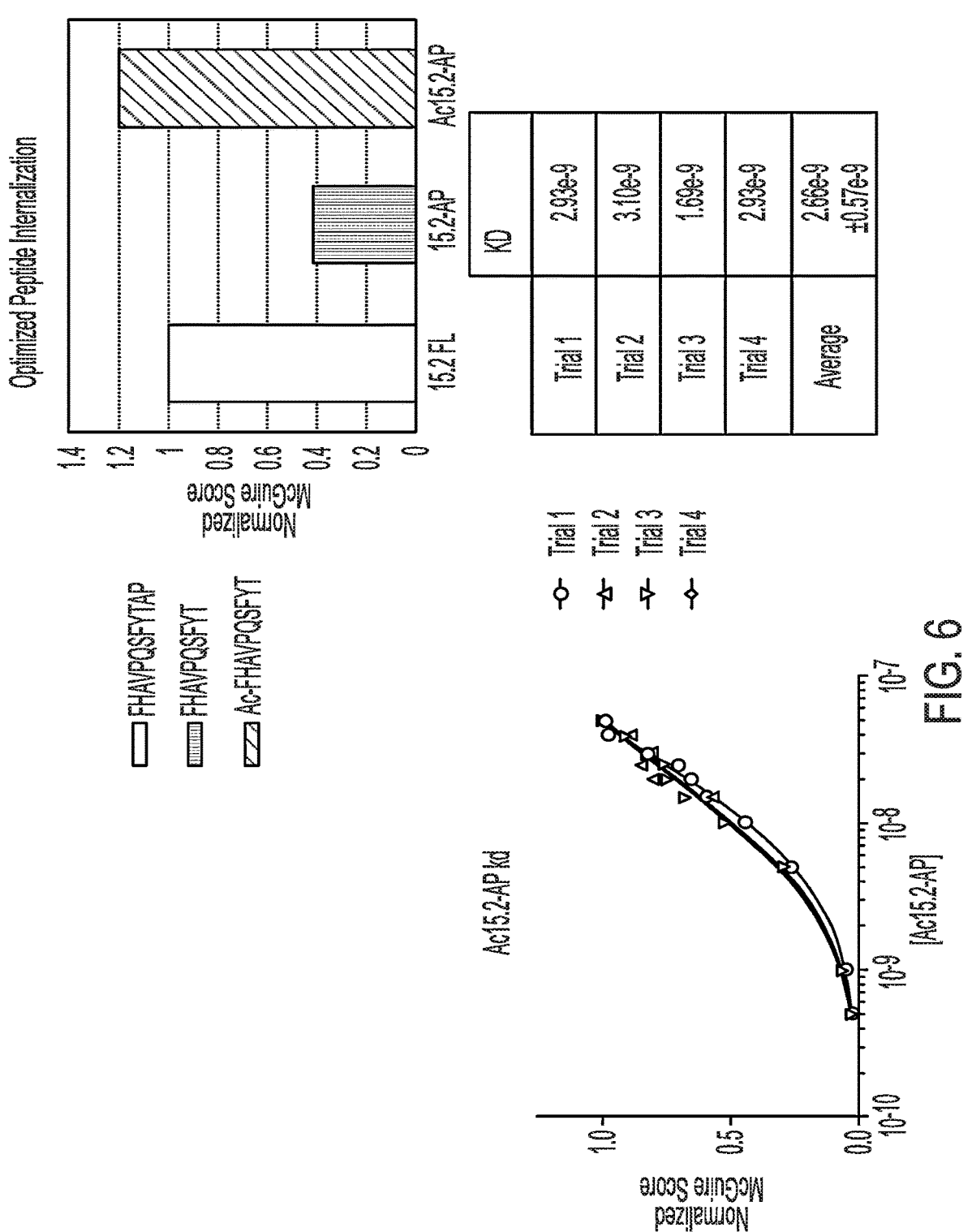
FIG. 6 shows that acetylation improves binding of the truncated peptide (SEQ ID NO: 3, FHAVPQSFYTAP, SEQ ID NO: 1).

FIG. 6 shows that acetylation improves binding of the truncated peptide.

d. Example 4: Peptide Co-Localizes with the Lysosome

Figure 7:
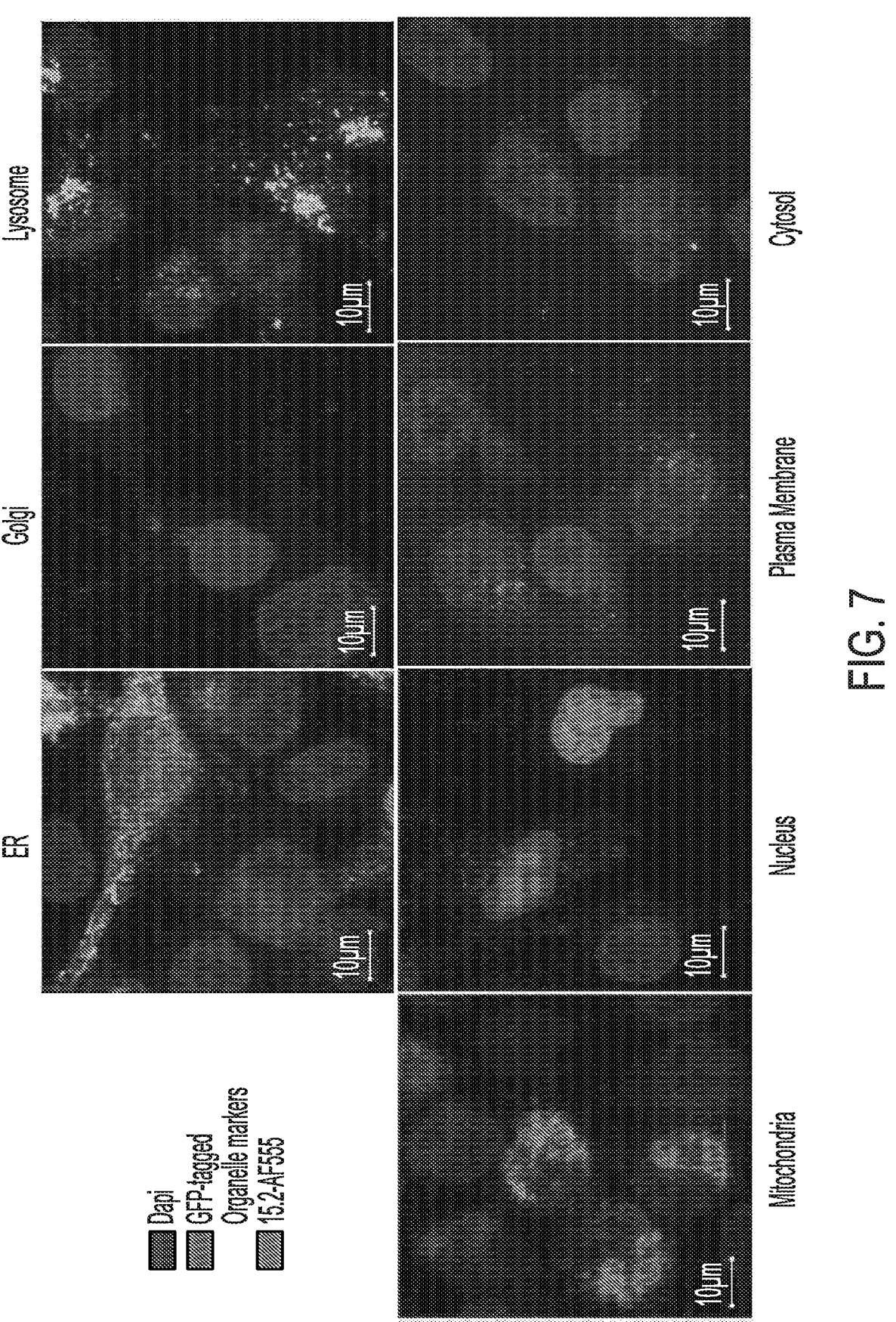
FIG. 7 shows that peptide co-localizes with the lysosome.
Figure 8:
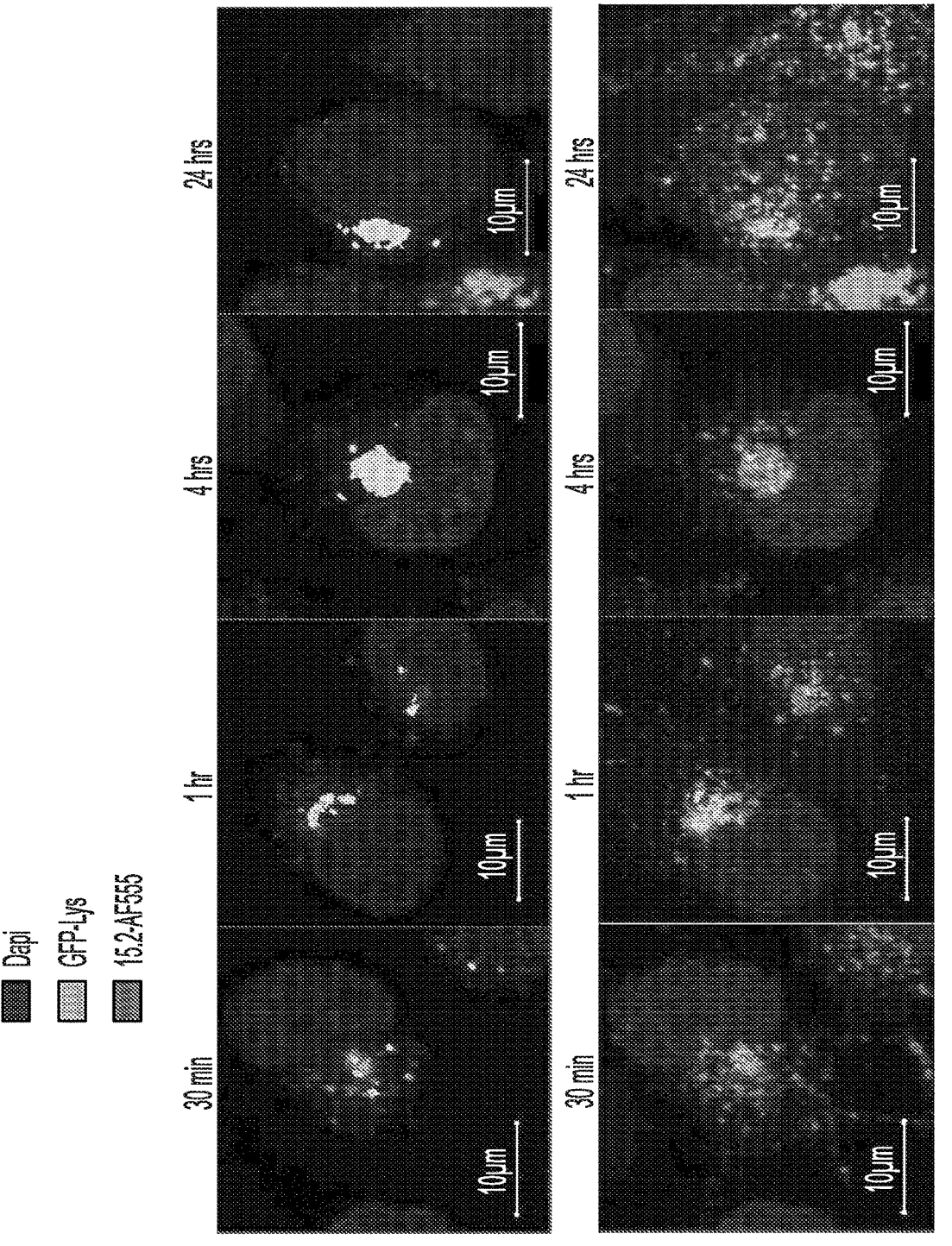
FIG. 8 shows that HCC15.2 accumulates in the lysosome over time.
Figure 16:
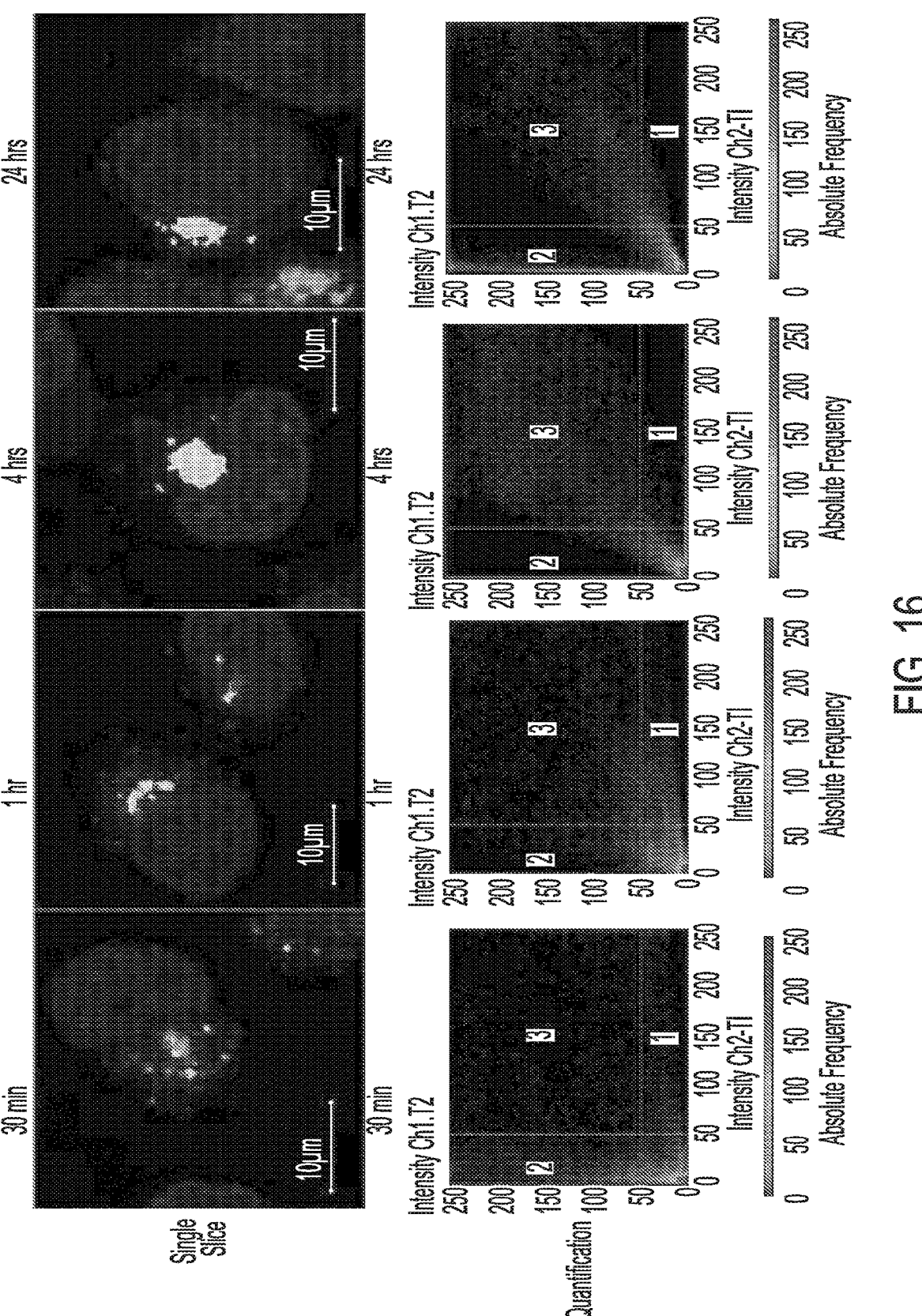
FIG. 16 shows that HCC15.2 accumulates in the lysosome over time.
Figure 16:
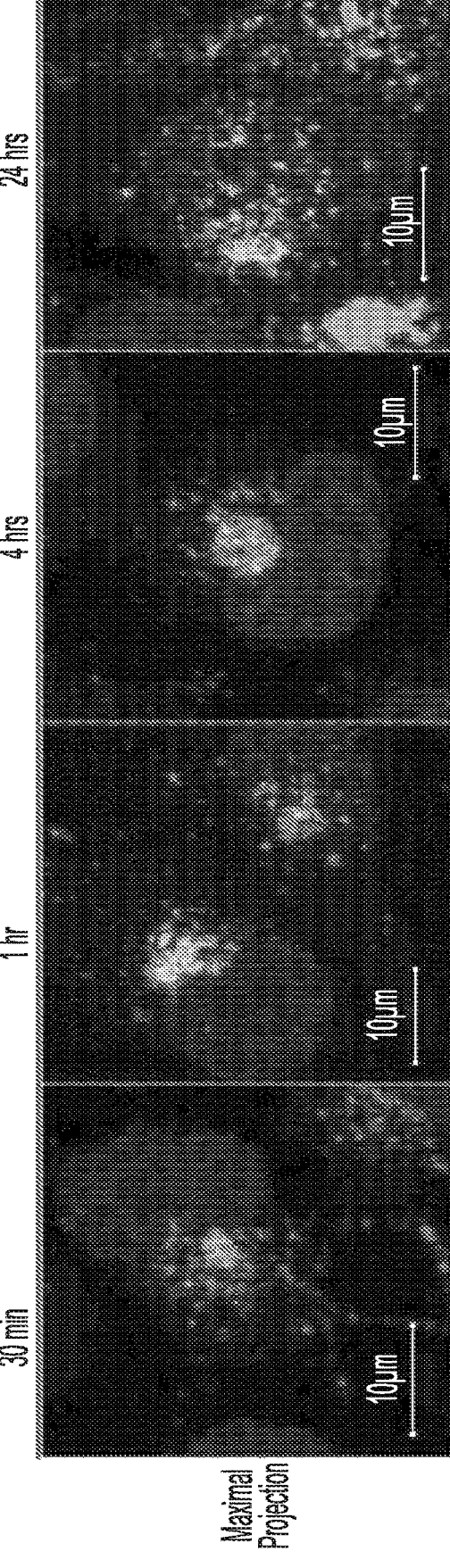

FIG. 7 shows that the MGS peptide co-localizes with the lysosome and accumulates in the lysosome over time (see, FIG. 8 and FIG. 16).

e. Example 5: HCC15.2 Conjugated to Saporin

Figure 9:
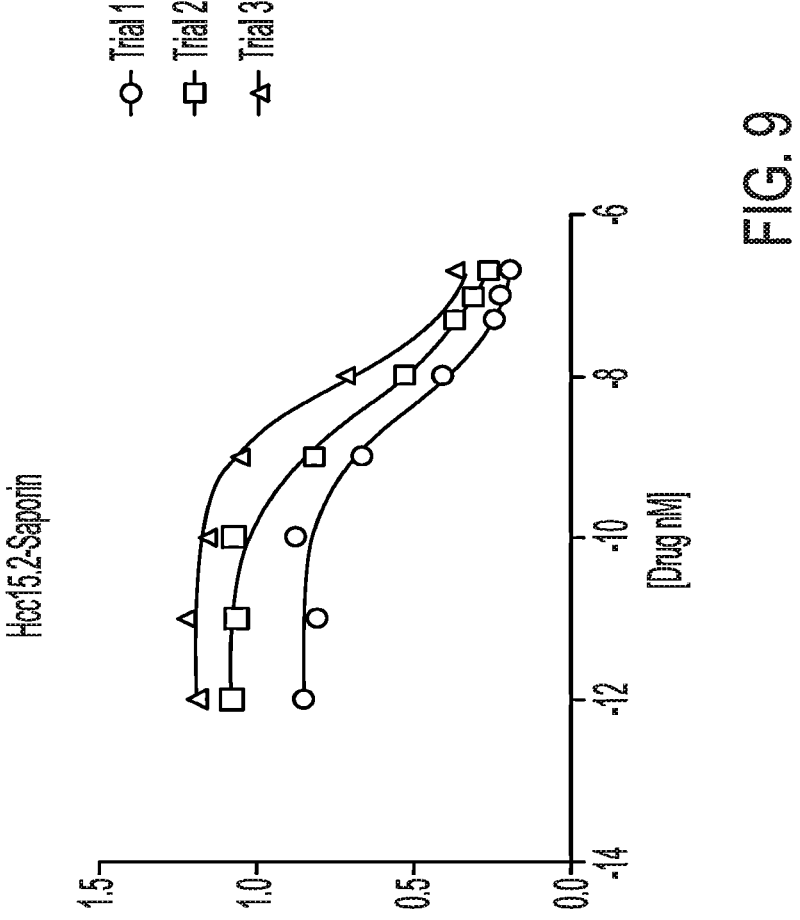
FIG. 9 shows that in vitro drug data of HCC15.2 conjugated to saporin.

Additional experiments were conducted to examine HCC15.2 conjugated to saporin in cell viability assays (see, FIG. 9 and Table 2). For this, tumor cell lines were plated on black-walled, clear flat-bottom, 96 well plates. The next day, media was replaced with a concentration gradient of Hcc15.2-Saporin, Saporin alone, or no treatment. After 1 hr incubation, treatment was removed and replaced with culture media. 72 hours later cell viability was measured using Cell Titer Glo® and luminescence was measured on an Analyst HT from LjL Biosystems. IC50s were calculated on Graphpad Prizm.

Figure 21:
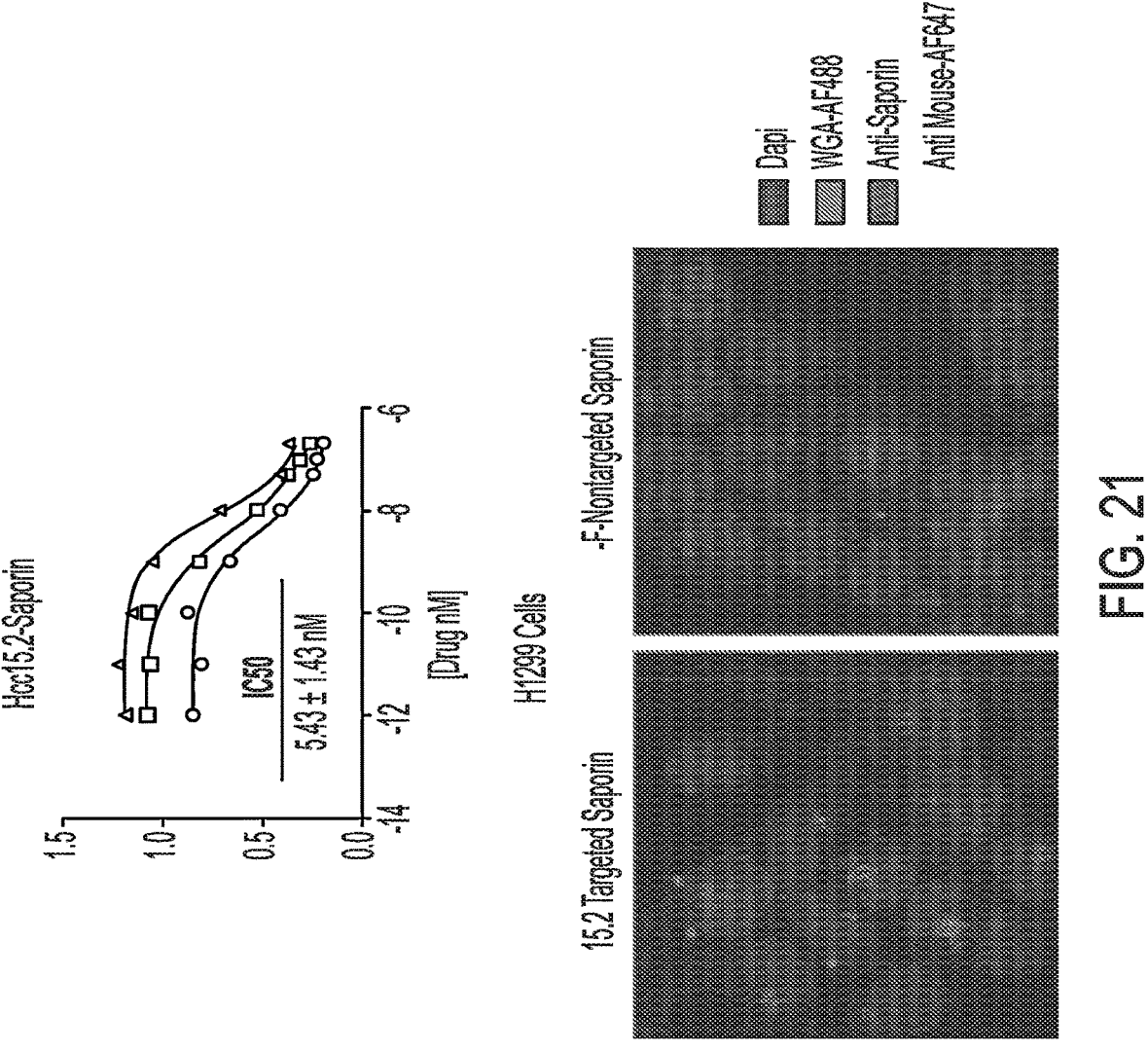
FIG. 21 shows that HCC15.2 targets saporin to cancer cells in vitro.
Figure 22:
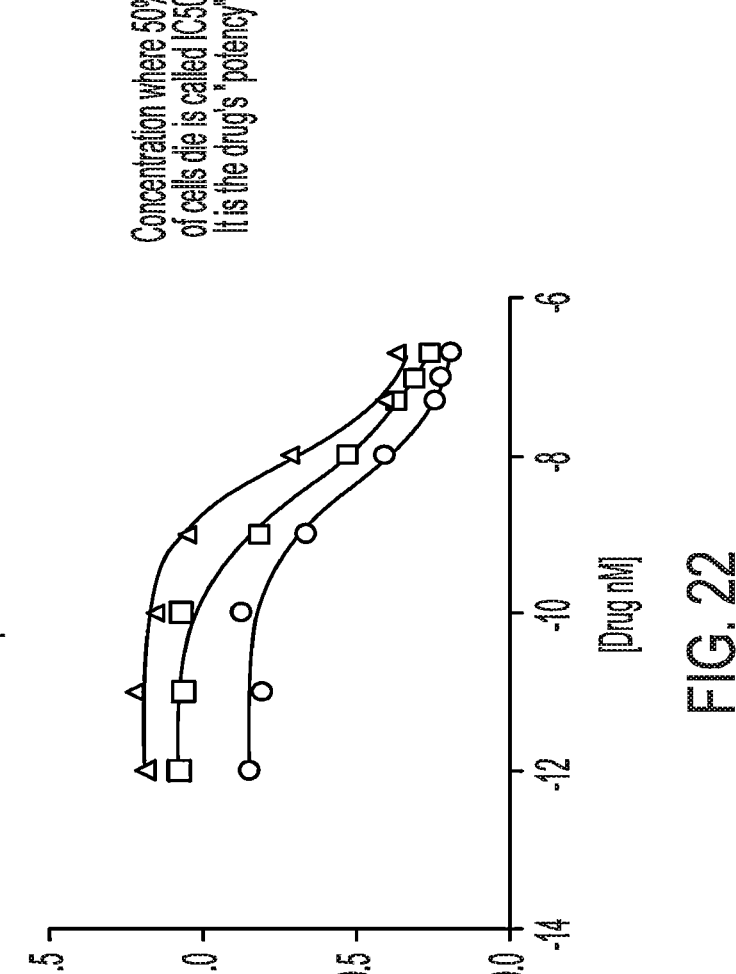
FIG. 22 is an example of the cancer cell killing assay showing that HCC15.2 targets saporin to cancer cells in vitro.

A cancer cell killing assay was performed (see, FIG. 22). Cancer cells were put into a dish. After 24 hours, cells were given different doses of peptide-saporin for 1 hour. Peptide-saporin was washed off and cells were left for 72 more hours. Assay to measure live cells performed. FIG. 21 shows that HCC15.2 targets saporin to cancer cells in vitro. These results demonstrate that saporin did not enter the cell by itself, however, saporin did enter the cell when conjugated to a required MGS peptide (e.g., HCC15.2). The results also show that HCC15.2-saporin lowers off target effects and escapes intracellular vesicles.

TABLE 2

| | Cell viability in multiple cell lines. | | |
| --- | --- | --- | --- |
| Cell Line | Peptide Drug | # of Repeats | Average KD |
| H1299 | 15.2-Saporin | 3 | 4.97e−09 |
| | Control-Saporin | 2 | 1.05e−09 |
| H2009 | 15.2-Saporin | 2 | 5.55e−09 |
| | Control-Saporin | 2 | 2.43e−07 |
| HBEC | 15.2-Saporin | 2 | 2.58e−07 |
| | Control-Saporin | 1 | 4.18e−07 |

FIG. 10 shows that HCC15.2 conjugated to saporin reduces tumor growth in a human NSCLC xenograft model compared to free-saporin.

Figure 13:
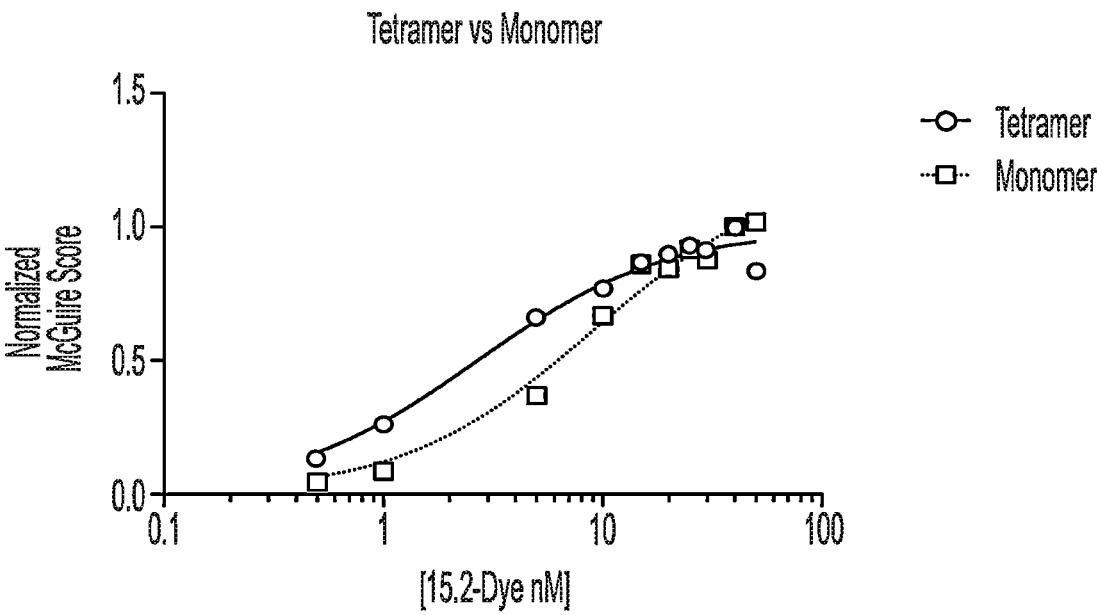
FIG. 13 is a line graph showing the flow cytometry results to measure KD.
Figure 14:
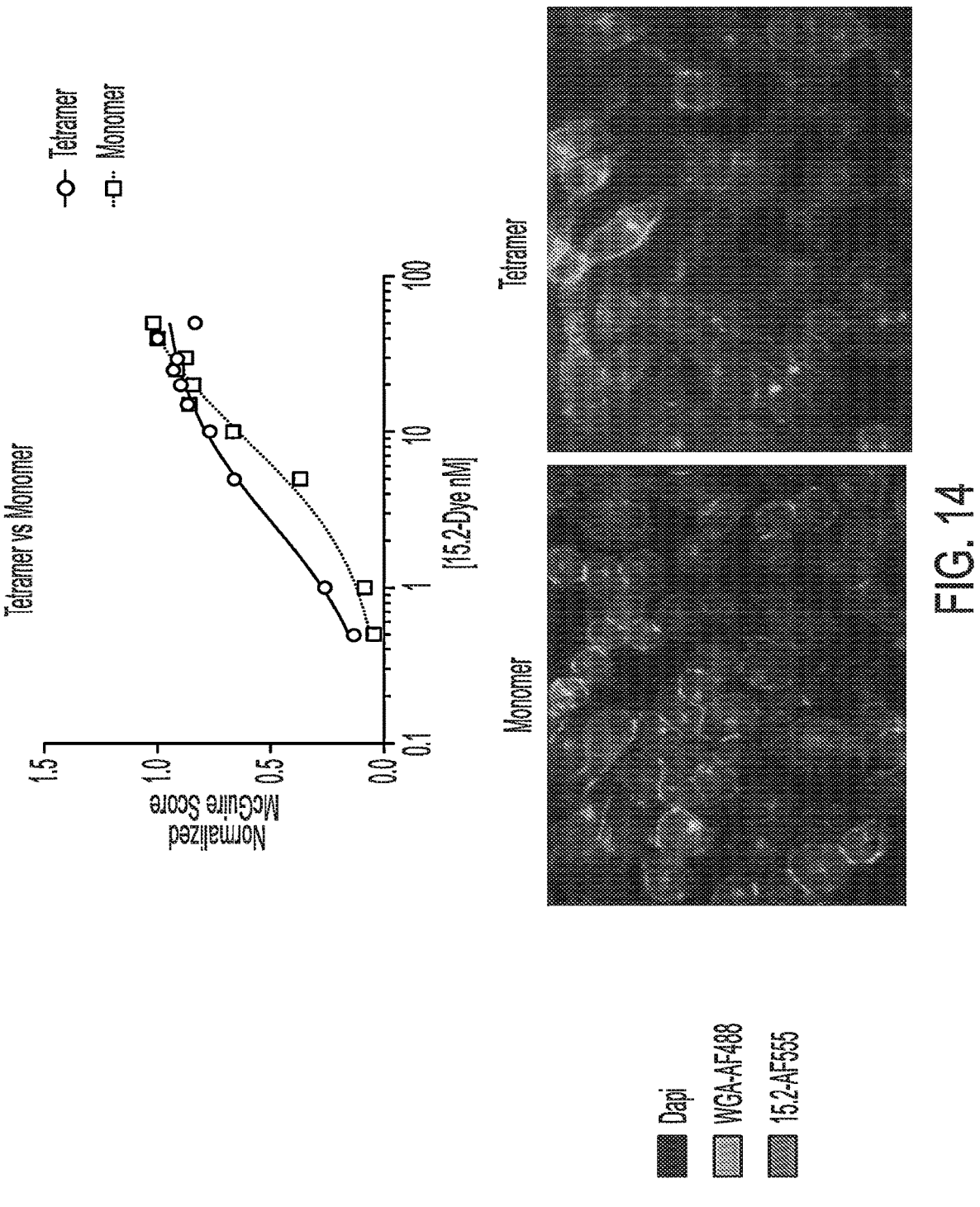
FIG. 14 shows that tetramerization does not significantly improve half maximal binding.

Example 6: Tetramerization does not Significantly Improve Half Maximal Binding Flow cytometry is carried out to measure KD. Cells are treated with increasing concentrations of peptide-dye for one hour. MGS peptide(s) that enter or go into the cells, take the dye with it. Cells are washed and placed in a tube to run flow cytometry. The flow cytometer can measure brightness of 10,000 or more individual cells. Each concentration is quantified and plotted (see, FIGS. 13 and 14). The curves are mathematically fitted to data and the halfway point is KD (e.g., a measure of how good the binding is).

Example 7: HCC15.2-Targeted NIR Dye Accumulates into Tumors In Vivo

In Vivo Imaging. H2009 tumor cells were suspended in 106 cells/100 μl sterile PBS and were injected subcutaneously on the flank of female athymic nude mice (Jackson Labs.) Cysteine labeled peptides were conjugated to maleimide Alexafluor-750 C5 (1:1.1) in sterile PBS pH 7.4 for 1 hour. Peptide-dye conjugate was diluted in sterile PBS to 15 μg dye per 100 μl and 100 ul were injected intravenously via lateral tail vein into 4 mice/group. Mice were anesthetized with Isothesia and whole animal images were collected on an IVIS at 12, 24, 48, and 72 hours. Ex vivo tumors and organs were then weighed and imaged at 72 hours.

Figure 17:
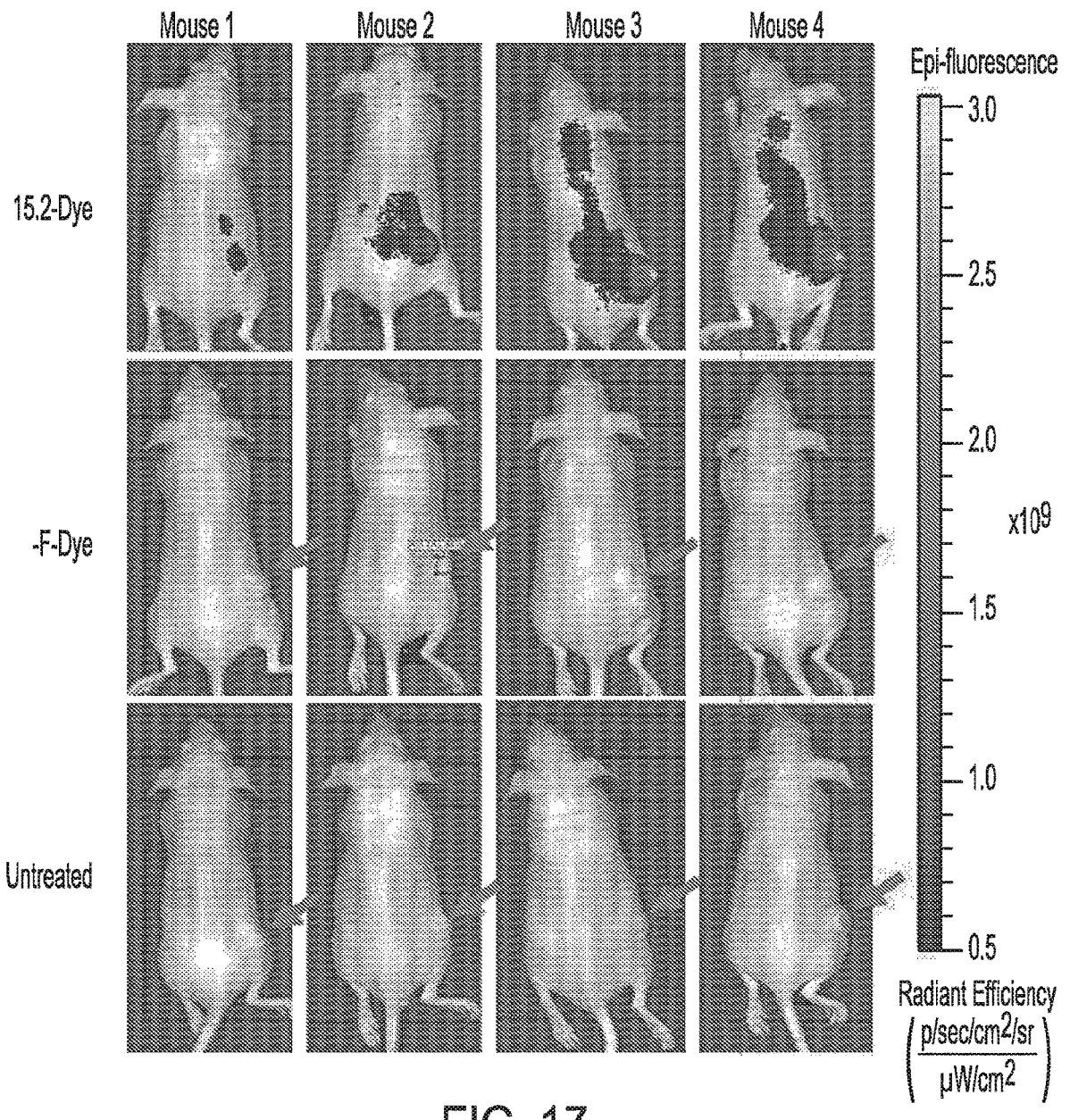
FIG. 17 shows that HCC15.2-targeted NIR dye accumulates into tumors in vivo.
Figure 20:
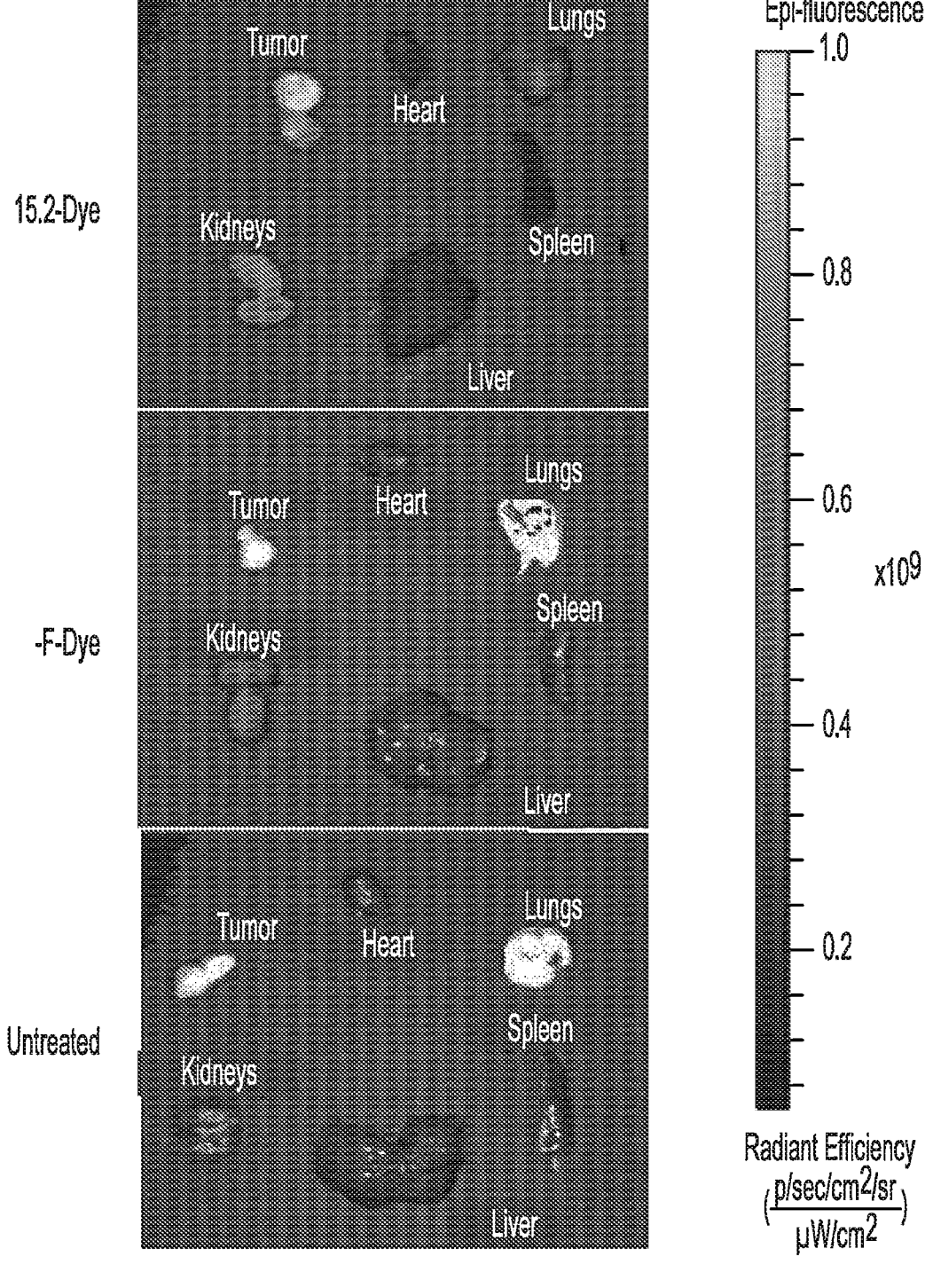
FIG. 20 shows the results of ex vivo imaging of organs.
Figure 20:
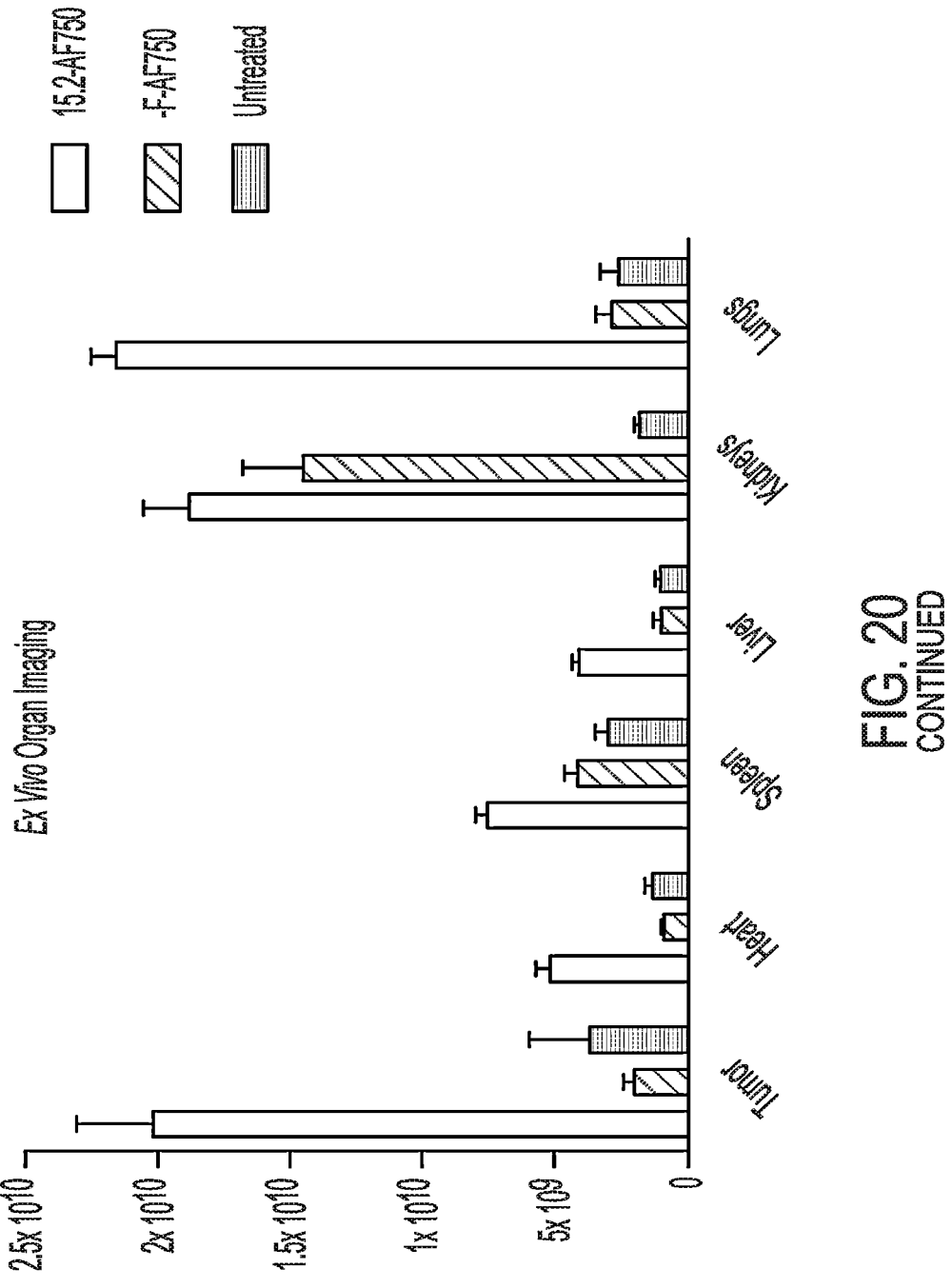

In vivo animal imaging studies were carried out. For these experiments, human cancer cells were placed under the skin of mice and allowed to grow a tumor to a certain size. Peptide with dye was injected by IV when tumors became a predetermined size. Animals were anesthetized and imaged at 12, 24, 48, and 72 hours. Organs and tumors were imaged at 72 hours. Yellow shows most peptide, maroon/red shows less peptide, no color is very little/no peptide. The HCC15.2-targeted NIR dye accumulates into tumors (see, FIG. 17) and is retained in the tumor over time (see, FIG. 18). FIGS. 19 and 20 show the results of ex vivo imaging.

Subcutaneous Tumor Growth Assay. H2009 tumors were established subcutaneously on the flank of athymic nude mice (Jackson Labs). Saporin conjugated to Streptavidin (SAZAP) was purchased from Advanced Targeting Systems and conjugated 1:1 with optimized, biotinylated Hcc15.2 and control peptides. When the tumors reached ~1003 mM in size, mice were injected with nontargeted saporin (no MGS peptide), 15.2-saporin conjugate, or nothing via lateral tail vein IV. Targeted and nontargeted saporin toxin was administered 2×/week for 2.5 weeks at ~7 ug/dose. Tumors were blindly measured every other day with calipers and tumor volumes were calculated using the equation π/6* (length*width)^3/2.

For the next set of experiments, human cancer cells were placed under the skin of mice and allowed to grow a tumor to a certain and predetermined size. The peptide conjugated or linked to saporin was injected by IV when tumors reached the predetermined size. Animals received 5 doses over 2.5 weeks of 7 or 7.5 μg/dose. Tumors were measured every other day. FIG. 23 shows that HCC15.2 targeting of saporin markedly slowed tumor growth.

Example 8: Further Characterization of the H1299.3 Peptide

A modified MGS peptide (SEQ ID NO: 31) that fuses amino acids 1-5 and 11-20 of the original MGS peptide: LQWRRNFGVWARYRL (SEQ ID NO: 31) was assessed. This MGS peptide maintains its cancer specificity and increases its ability to traffic to the autophagosome. Acetylation protects degradation in vivo and improves solubility. This MGS peptide hones to a NSCLC tumor in an animal (see, FIG. 27). The data show that no tumor targeting was observed for the nonacetylated version, This MGS peptide (e.g., the modified 15-mer) has >2-fold reduction in heart, lung and kidney tumors (see, FIG. 27). 1299.3 Ac-15mer cell binding results are shown in FIG. 28.

Cell Culture. Human NSCLC lines were provided. Cells were cultured in RPMI 1640 with L-glutamine and 5% FBS at 37° C. and 5% CO2.

Example 9: In Vitro Delivery of Saporin with Other Peptides

Figures 28, 29:
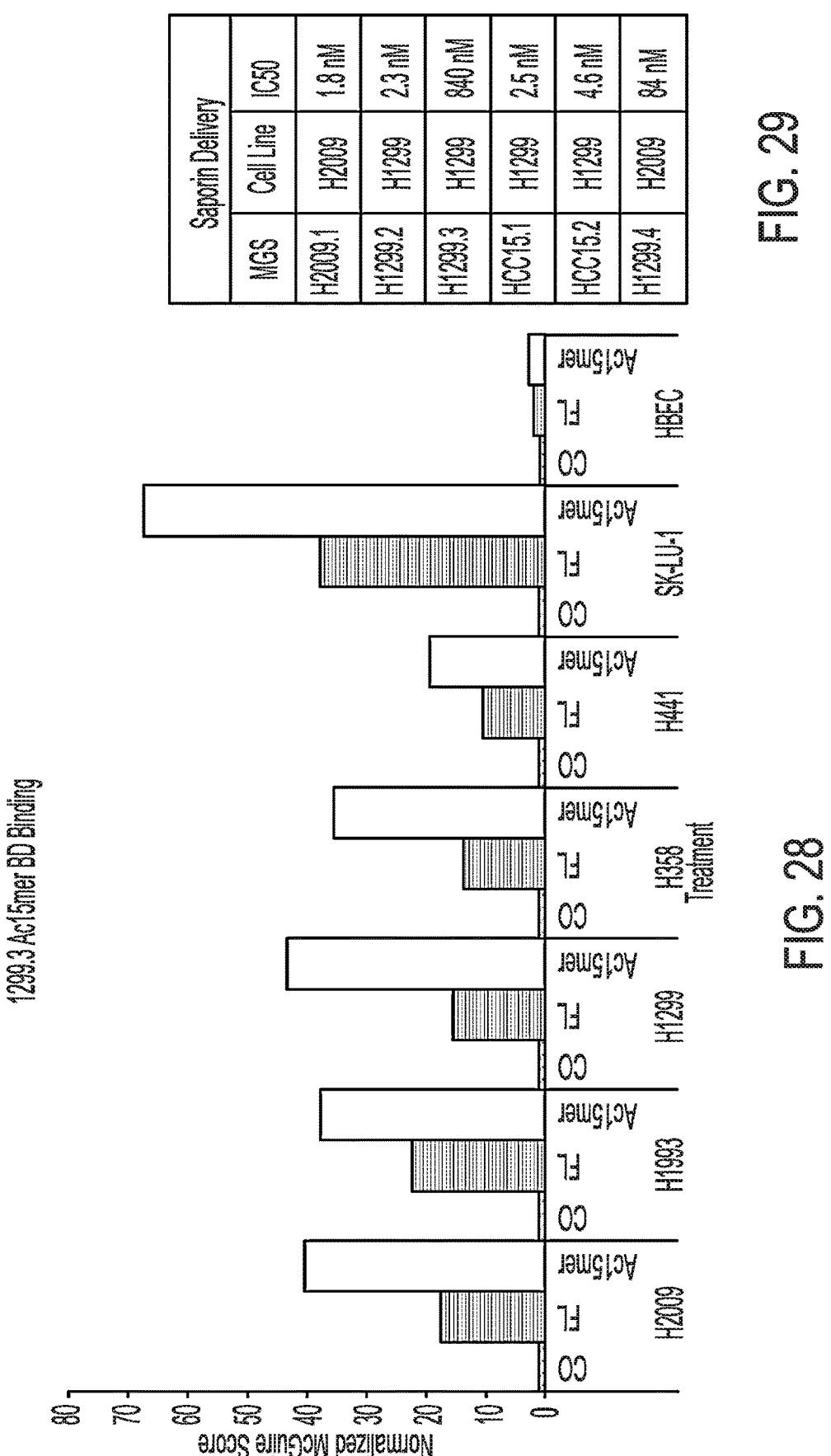
FIG. 28 is a bar graph showing 1299.3 Ac-15mer cancer cell binding compared to normal cell binding.
FIG. 29 is a table showing saporin delivery in vitro with other peptides (parental peptide not optimized except for HCC15.2).

FIG. 29 shows the IC50 in various cell lines of the administration of saporin conjugated or linked to select MGS peptides.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A molecular guidance system (MGS) peptide of amino acid sequence selected from CH$_3$CO-FHAVPQSFYT-PEG$_{11}$-C-NH$_2$ (SEQ ID No: 76), and FHAVPQSFY (SEQ ID NO: 78).

2. The MGS peptide of claim 1, wherein the MGS peptide is covalently attached to a cytotoxic agent, directly or through a linker.

3. The MGS peptide of claim 2, wherein the linker comprises polyethylene glycol (PEG).

4. The MGS peptide of claim 3, wherein the cytotoxic agent comprises saporin and is covalently attached to PEG, directly or through a linker.

5. A composition comprising one or more cytotoxic agents conjugated to one or more molecular guidance system (MGS) peptides selected from:

LQWRRNFGVWARYRL (SEQ ID NO: 31), $CH_3CO$-LQWRRNFGVWARYRL, $CH_3CO$-LQWRRNFGVWARYRL-$PEG_{11}$-C-$NH_2$ (SEQ ID NO: 72), $CH_3CO$-FHAVPQSFYT-$PEG_{11}$-C-$NH_2$ (SEQ ID NO: 76), FHAVPQSFY (SEQ ID NO: 78), and $CH_3CO$-YAAWPASGAWT-$PEG_{11}$-C-$NH_2$ (SEQ ID NO: 71).

6. The composition of claim 5, wherein the composition comprises two MGS peptides conjugated to the one or more cytotoxic agents via one or more chemical linkers, wherein the one or more chemical linkers are covalently linked to one another to form a dimeric structure, and wherein the MGS peptides are not directly linked to each other.

7. The composition of claim 5, wherein the composition comprises four MGS peptides conjugated to the one or more cytotoxic agents via one or more chemical linkers, wherein the one or more chemical linkers are covalently linked to one another and form a tetrameric structure, and wherein the MGS peptides are not directly linked to each other.

8. The composition of claim 5, wherein the composition is a pharmaceutical composition further comprising a pharmaceutically acceptable carrier.

\*  \*  \*  \*  \*

SEQUENCE LISTING

```
Sequence total quantity: 84
SEQ ID NO: 1              moltype = AA   length = 12
FEATURE                   Location/Qualifiers
REGION                    1..12
                          note = Synthetic construct
source                    1..12
                          mol_type = protein
                          organism = synthetic construct
SEQUENCE: 1
FHAVPQSFYT AP                                                12

SEQ ID NO: 2              moltype = AA   length = 11
FEATURE                   Location/Qualifiers
REGION                    1..11
                          note = Synthetic construct
source                    1..11
                          mol_type = protein
                          organism = synthetic construct
SEQUENCE: 2
FHAVPQSFYT A                                                 11

SEQ ID NO: 3              moltype = AA   length = 10
FEATURE                   Location/Qualifiers
REGION                    1..10
                          note = Synthetic Construct
source                    1..10
```

```
                          mol_type = protein
                          organism = synthetic construct
SEQUENCE: 3
FHAVPQSFYT                                                              10

SEQ ID NO: 4              moltype = AA  length = 20
FEATURE                   Location/Qualifiers
REGION                    1..20
                          note = Synthetic Construct
source                    1..20
                          mol_type = protein
                          organism = synthetic construct
SEQUENCE: 4
VSQTMRQTAV PLLWFWTGSL                                                   20

SEQ ID NO: 5              moltype = AA  length = 20
FEATURE                   Location/Qualifiers
REGION                    1..20
                          note = Synthetic construct
source                    1..20
                          mol_type = protein
                          organism = synthetic construct
SEQUENCE: 5
YAAWPASGAW TGTAPCSAGT                                                   20

SEQ ID NO: 6              moltype = AA  length = 11
FEATURE                   Location/Qualifiers
REGION                    1..11
                          note = Synthetic construct
source                    1..11
                          mol_type = protein
                          organism = synthetic construct
SEQUENCE: 6
YAAWPASGAW T                                                            11

SEQ ID NO: 7              moltype = AA  length = 20
FEATURE                   Location/Qualifiers
REGION                    1..20
                          note = Synthetic construct
source                    1..20
                          mol_type = protein
                          organism = synthetic construct
SEQUENCE: 7
RGDLATLRQL AQEDGVVGVR                                                   20

SEQ ID NO: 8              moltype = AA  length = 11
FEATURE                   Location/Qualifiers
REGION                    1..11
                          note = Synthetic construct
MOD_RES                   1
                          note = D-Leucine
source                    1..11
                          mol_type = protein
                          organism = synthetic construct
SEQUENCE: 8
LRGDLATLRQ L                                                            11

SEQ ID NO: 9              moltype = AA  length = 20
FEATURE                   Location/Qualifiers
REGION                    1..20
                          note = Synthetic construct
source                    1..20
                          mol_type = protein
                          organism = synthetic construct
SEQUENCE: 9
EAMNSAEQSA AVVQWEKRRI                                                   20

SEQ ID NO: 10             moltype = AA  length = 20
FEATURE                   Location/Qualifiers
REGION                    1..20
                          note = Synthetic construct
source                    1..20
                          mol_type = protein
                          organism = synthetic construct
SEQUENCE: 10
ATEPRKQYAT PRVFWTDAPG                                                   20

SEQ ID NO: 11             moltype = AA  length = 20
FEATURE                   Location/Qualifiers
```

-continued

```
REGION                   1..20
                         note = Synthetic construct
source                   1..20
                         mol_type = protein
                         organism = synthetic construct
SEQUENCE: 11
MTVCNASQRQ AHAQATAVSL                                         20

SEQ ID NO: 12            moltype = AA  length = 20
FEATURE                  Location/Qualifiers
REGION                   1..20
                         note = Synthetic construct
source                   1..20
                         mol_type = protein
                         organism = synthetic construct
SEQUENCE: 12
MRGQTGKLPT EHFTDTGVAF                                         20

SEQ ID NO: 13            moltype = AA  length = 20
FEATURE                  Location/Qualifiers
REGION                   1..20
                         note = Synthetic construct
source                   1..20
                         mol_type = protein
                         organism = synthetic construct
SEQUENCE: 13
MTGKAAAPHQ EDRHANGLEQ                                         20

SEQ ID NO: 14            moltype = AA  length = 19
FEATURE                  Location/Qualifiers
REGION                   1..19
                         note = Synthetic construct
source                   1..19
                         mol_type = protein
                         organism = synthetic construct
SEQUENCE: 14
TNSCRGDWLC DAVPEKARV                                          19

SEQ ID NO: 15            moltype = AA  length = 16
FEATURE                  Location/Qualifiers
REGION                   1..16
                         note = Synthetic construct
source                   1..16
                         mol_type = protein
                         organism = synthetic construct
SEQUENCE: 15
EHPWFNMWSW ATQVQE                                             16

SEQ ID NO: 16            moltype = AA  length = 20
FEATURE                  Location/Qualifiers
REGION                   1..20
                         note = Synthetic construct
source                   1..20
                         mol_type = protein
                         organism = synthetic construct
SEQUENCE: 16
YPGSPTQYPS SMHEYHSSSE                                         20

SEQ ID NO: 17            moltype = AA  length = 20
FEATURE                  Location/Qualifiers
REGION                   1..20
                         note = Synthetic construct
source                   1..20
                         mol_type = protein
                         organism = synthetic construct
SEQUENCE: 17
AHTIDDEWAS YHMQQWNSPP                                         20

SEQ ID NO: 18            moltype = AA  length = 20
FEATURE                  Location/Qualifiers
REGION                   1..20
                         note = Synthetic construct
source                   1..20
                         mol_type = protein
                         organism = synthetic construct
SEQUENCE: 18
FEEFYSRQSN TIPYPQQYKG                                         20

SEQ ID NO: 19            moltype = AA  length = 20
```

-continued

```
FEATURE                 Location/Qualifiers
REGION                  1..20
                        note = Synthetic construct
source                  1..20
                        mol_type = protein
                        organism = synthetic construct
SEQUENCE: 19
THGNKHQSWT YPSEINHKNY                                                 20

SEQ ID NO: 20           moltype = AA   length = 21
FEATURE                 Location/Qualifiers
REGION                  1..21
                        note = Synthetic construct
source                  1..21
                        mol_type = protein
                        organism = synthetic construct
SEQUENCE: 20
NLADTWTQTQ QHDFHVLRGT R                                               21

SEQ ID NO: 21           moltype = AA   length = 16
FEATURE                 Location/Qualifiers
REGION                  1..16
                        note = Synthetic construct
source                  1..16
                        mol_type = protein
                        organism = synthetic construct
SEQUENCE: 21
GYSWWQPNWP SSTWDT                                                     16

SEQ ID NO: 22           moltype = AA   length = 19
FEATURE                 Location/Qualifiers
REGION                  1..19
                        note = Synthetic construct
source                  1..19
                        mol_type = protein
                        organism = synthetic construct
SEQUENCE: 22
EHPWFNMWSW ATQVQEKKK                                                  19

SEQ ID NO: 23           moltype = AA   length = 20
FEATURE                 Location/Qualifiers
REGION                  1..20
                        note = Synthetic construct
source                  1..20
                        mol_type = protein
                        organism = synthetic construct
SEQUENCE: 23
NLADTWTQTQ QHDFHVLRGT                                                 20

SEQ ID NO: 24           moltype = AA   length = 20
FEATURE                 Location/Qualifiers
REGION                  1..20
                        note = Synthetic construct
source                  1..20
                        mol_type = protein
                        organism = synthetic construct
SEQUENCE: 24
SVEYWGERMY YDVMESLGFS                                                 20

SEQ ID NO: 25           moltype = AA   length = 20
FEATURE                 Location/Qualifiers
REGION                  1..20
                        note = Synthetic construct
source                  1..20
                        mol_type = protein
                        organism = synthetic construct
SEQUENCE: 25
FAAKRAEWWD PGQLWDAVWN                                                 20

SEQ ID NO: 26           moltype = AA   length = 20
FEATURE                 Location/Qualifiers
REGION                  1..20
                        note = Synthetic construct
source                  1..20
                        mol_type = protein
                        organism = synthetic construct
SEQUENCE: 26
QEALEEWFWK MMPWSGPSGQ                                                 20
```

-continued

```
SEQ ID NO: 27          moltype = AA   length = 20
FEATURE                Location/Qualifiers
REGION                 1..20
                       note = Synthetic construct
source                 1..20
                       mol_type = protein
                       organism = synthetic construct
SEQUENCE: 27
TWTDFGQWPW PFGAEGTRAF                                       20

SEQ ID NO: 28          moltype = AA   length = 20
FEATURE                Location/Qualifiers
REGION                 1..20
                       note = Synthetic construct
source                 1..20
                       mol_type = protein
                       organism = synthetic construct
SEQUENCE: 28
MDGATWWTQL DPLLVWEGET                                       20

SEQ ID NO: 29          moltype = AA   length = 20
FEATURE                Location/Qualifiers
REGION                 1..20
                       note = Synthetic construct
source                 1..20
                       mol_type = protein
                       organism = synthetic construct
SEQUENCE: 29
SADWFQGPAE WLLEGWMGPL                                       20

SEQ ID NO: 30          moltype = AA   length = 20
FEATURE                Location/Qualifiers
REGION                 1..20
                       note = Synthetic construct
source                 1..20
                       mol_type = protein
                       organism = synthetic construct
SEQUENCE: 30
LQWRRDDNVH NFGVWARYRL                                       20

SEQ ID NO: 31          moltype = AA   length = 15
FEATURE                Location/Qualifiers
REGION                 1..15
                       note = Synthetic construct
source                 1..15
                       mol_type = protein
                       organism = synthetic construct
SEQUENCE: 31
LQWRRNFGVW ARYRL                                            15

SEQ ID NO: 32          moltype = AA   length = 20
FEATURE                Location/Qualifiers
REGION                 1..20
                       note = Synthetic construct
source                 1..20
                       mol_type = protein
                       organism = synthetic construct
SEQUENCE: 32
ATEPRKQYAT PRVFWTDAPG                                       20

SEQ ID NO: 33          moltype = AA   length = 11
FEATURE                Location/Qualifiers
REGION                 1..11
                       note = Synthetic construct
source                 1..11
                       mol_type = protein
                       organism = synthetic construct
SEQUENCE: 33
KQYATPRVFW T                                                11

SEQ ID NO: 34          moltype = AA   length = 20
FEATURE                Location/Qualifiers
REGION                 1..20
                       note = Synthetic construct
source                 1..20
                       mol_type = protein
                       organism = synthetic construct
SEQUENCE: 34
VSQTMRQTAV PLLWFWTGSL                                       20
```

-continued

```
SEQ ID NO: 35           moltype = AA   length = 20
FEATURE                 Location/Qualifiers
REGION                  1..20
                        note = Synthetic construct
source                  1..20
                        mol_type = protein
                        organism = synthetic construct
SEQUENCE: 35
YAAWPASGAW TGTAPCSAGT                                        20

SEQ ID NO: 36           moltype = AA   length = 20
FEATURE                 Location/Qualifiers
REGION                  1..20
                        note = Synthetic construct
source                  1..20
                        mol_type = protein
                        organism = synthetic construct
SEQUENCE: 36
LQWRRDDNVH NFGVWARYRL                                        20

SEQ ID NO: 37           moltype = AA   length = 20
FEATURE                 Location/Qualifiers
REGION                  1..20
                        note = Synthetic construct
source                  1..20
                        mol_type = protein
                        organism = synthetic construct
SEQUENCE: 37
RGDLATLRQL AQEDGVVGVR                                        20

SEQ ID NO: 38           moltype = AA   length = 16
FEATURE                 Location/Qualifiers
REGION                  1..16
                        note = Synthetic construct
source                  1..16
                        mol_type = protein
                        organism = synthetic construct
SEQUENCE: 38
EHPWFNMWSW ATQVQE                                            16

SEQ ID NO: 39           moltype = AA   length = 20
FEATURE                 Location/Qualifiers
REGION                  1..20
                        note = Synthetic construct
source                  1..20
                        mol_type = protein
                        organism = synthetic construct
SEQUENCE: 39
YPGSPTQYPS SMHEYHSSSE                                        20

SEQ ID NO: 40           moltype = AA   length = 20
FEATURE                 Location/Qualifiers
REGION                  1..20
                        note = Synthetic construct
source                  1..20
                        mol_type = protein
                        organism = synthetic construct
SEQUENCE: 40
AHTIDDEWAS YHMQQWNSPP                                        20

SEQ ID NO: 41           moltype = AA   length = 20
FEATURE                 Location/Qualifiers
REGION                  1..20
                        note = Synthetic construct
source                  1..20
                        mol_type = protein
                        organism = synthetic construct
SEQUENCE: 41
FEEFYSRQSN TIPYPQQYKG                                        20

SEQ ID NO: 42           moltype = AA   length = 20
FEATURE                 Location/Qualifiers
REGION                  1..20
                        note = Synthetic construct
source                  1..20
                        mol_type = protein
                        organism = synthetic construct
SEQUENCE: 42
```

-continued

```
ATEPRKQYAT PRVFWTDAPG                                                 20

SEQ ID NO: 43           moltype = AA  length = 12
FEATURE                 Location/Qualifiers
REGION                  1..12
                        note = Synthetic construct
source                  1..12
                        mol_type = protein
                        organism = synthetic construct
SEQUENCE: 43
FHAVPQSFYT AP                                                         12

SEQ ID NO: 44           moltype = AA  length = 20
FEATURE                 Location/Qualifiers
REGION                  1..20
                        note = Synthetic construct
source                  1..20
                        mol_type = protein
                        organism = synthetic construct
SEQUENCE: 44
EAMNSAEQSA AVVQWEKRRI                                                 20

SEQ ID NO: 45           moltype = AA  length = 20
FEATURE                 Location/Qualifiers
REGION                  1..20
                        note = Synthetic construct
source                  1..20
                        mol_type = protein
                        organism = synthetic construct
SEQUENCE: 45
MTVCNASQRQ AHAQATAVSL                                                 20

SEQ ID NO: 46           moltype = AA  length = 20
FEATURE                 Location/Qualifiers
REGION                  1..20
                        note = Synthetic construct
source                  1..20
                        mol_type = protein
                        organism = synthetic construct
SEQUENCE: 46
LTVHGRGPEY NPSWNRRAFP                                                 20

SEQ ID NO: 47           moltype = AA  length = 20
FEATURE                 Location/Qualifiers
REGION                  1..20
                        note = Synthetic construct
source                  1..20
                        mol_type = protein
                        organism = synthetic construct
SEQUENCE: 47
SVEYWGERMY YDVMESLGFS                                                 20

SEQ ID NO: 48           moltype = AA  length = 20
FEATURE                 Location/Qualifiers
REGION                  1..20
                        note = Synthetic construct
source                  1..20
                        mol_type = protein
                        organism = synthetic construct
SEQUENCE: 48
FAAKRAEWWD PGQLWDAVWN                                                 20

SEQ ID NO: 49           moltype = AA  length = 20
FEATURE                 Location/Qualifiers
REGION                  1..20
                        note = Synthetic construct
source                  1..20
                        mol_type = protein
                        organism = synthetic construct
SEQUENCE: 49
QEALEEWFWK MMPWSGPSGQ                                                 20

SEQ ID NO: 50           moltype = AA  length = 20
FEATURE                 Location/Qualifiers
REGION                  1..20
                        note = Synthetic construct
source                  1..20
                        mol_type = protein
                        organism = synthetic construct
```

```
SEQUENCE: 50
TWTDFGQWPW PFGAEGTRAF                                                    20

SEQ ID NO: 51            moltype = AA  length = 20
FEATURE                  Location/Qualifiers
REGION                   1..20
                         note = Synthetic construct
source                   1..20
                         mol_type = protein
                         organism = synthetic construct
SEQUENCE: 51
MDGATWWTQL DPLLVWEGET                                                    20

SEQ ID NO: 52            moltype = AA  length = 20
FEATURE                  Location/Qualifiers
REGION                   1..20
                         note = Synthetic construct
source                   1..20
                         mol_type = protein
                         organism = synthetic construct
SEQUENCE: 52
SADWFQGPAE WLLEGWMGPL                                                    20

SEQ ID NO: 53            moltype = AA  length = 20
FEATURE                  Location/Qualifiers
REGION                   1..20
                         note = Synthetic construct
source                   1..20
                         mol_type = protein
                         organism = synthetic construct
SEQUENCE: 53
MRGQTGKLPT EHFTDTGVAF                                                    20

SEQ ID NO: 54            moltype = AA  length = 20
FEATURE                  Location/Qualifiers
REGION                   1..20
                         note = Synthetic construct
source                   1..20
                         mol_type = protein
                         organism = synthetic construct
SEQUENCE: 54
MTGKAAAPHQ EDRHANGLEQ                                                    20

SEQ ID NO: 55            moltype = AA  length = 20
FEATURE                  Location/Qualifiers
REGION                   1..20
                         note = Synthetic construct
source                   1..20
                         mol_type = protein
                         organism = synthetic construct
SEQUENCE: 55
MEKLPLSKTG RTVSEGVSPP                                                    20

SEQ ID NO: 56            moltype = AA  length = 19
FEATURE                  Location/Qualifiers
REGION                   1..19
                         note = Synthetic construct
source                   1..19
                         mol_type = protein
                         organism = synthetic construct
SEQUENCE: 56
TNSCRGDWLC DAVPEKARV                                                     19

SEQ ID NO: 57            moltype = AA  length = 20
FEATURE                  Location/Qualifiers
REGION                   1..20
                         note = Synthetic construct
source                   1..20
                         mol_type = protein
                         organism = synthetic construct
SEQUENCE: 57
SAKTAVSQRV WLPSHRGGEP                                                    20

SEQ ID NO: 58            moltype = AA  length = 20
FEATURE                  Location/Qualifiers
REGION                   1..20
                         note = Synthetic construct
source                   1..20
                         mol_type = protein
```

```
                          organism = synthetic construct
SEQUENCE: 58
KSREHVNNSA CPSKRITAAL                                          20

SEQ ID NO: 59            moltype = AA   length = 20
FEATURE                  Location/Qualifiers
REGION                   1..20
                         note = Synthetic construct
source                   1..20
                         mol_type = protein
                         organism = synthetic construct
SEQUENCE: 59
WLSEAGPVVT VRALRGTGSW                                          20

SEQ ID NO: 60            moltype = AA   length = 20
FEATURE                  Location/Qualifiers
REGION                   1..20
                         note = Synthetic construct
source                   1..20
                         mol_type = protein
                         organism = synthetic construct
SEQUENCE: 60
TGGETSGIKK APYASTTRNR                                          20

SEQ ID NO: 61            moltype = AA   length = 20
FEATURE                  Location/Qualifiers
REGION                   1..20
                         note = Synthetic construct
source                   1..20
                         mol_type = protein
                         organism = synthetic construct
SEQUENCE: 61
SHHGVAGVDL GGGADFKSIA                                          20

SEQ ID NO: 62            moltype = AA   length = 24
FEATURE                  Location/Qualifiers
REGION                   1..24
                         note = Synthetic construct
source                   1..24
                         mol_type = protein
                         organism = synthetic construct
SEQUENCE: 62
SNSPLGLKDE ATQRLVLEQA KWLA                                     24

SEQ ID NO: 63            moltype = AA   length = 20
FEATURE                  Location/Qualifiers
REGION                   1..20
                         note = Synthetic construct
source                   1..20
                         mol_type = protein
                         organism = synthetic construct
SEQUENCE: 63
GPEDTSRAPE NQQKTFHRRW                                          20

SEQ ID NO: 64            moltype = AA   length = 22
FEATURE                  Location/Qualifiers
REGION                   1..22
                         note = Synthetic construct
source                   1..22
                         mol_type = protein
                         organism = synthetic construct
SEQUENCE: 64
SGETGSNLVG HELDFRPGSP SP                                       22

SEQ ID NO: 65            moltype = AA   length = 20
FEATURE                  Location/Qualifiers
REGION                   1..20
                         note = Synthetic construct
source                   1..20
                         mol_type = protein
                         organism = synthetic construct
SEQUENCE: 65
RYSPAATAEG RSVSKELLRV                                          20

SEQ ID NO: 66            moltype = AA   length = 20
FEATURE                  Location/Qualifiers
REGION                   1..20
                         note = Synthetic construct
source                   1..20
```

```
                              mol_type = protein
                              organism = synthetic construct
SEQUENCE: 66
GQELGAWTRS KGPEVQTSVL                                          20

SEQ ID NO: 67          moltype = AA   length = 20
FEATURE                Location/Qualifiers
REGION                 1..20
                       note = Synthetic construct
source                 1..20
                       mol_type = protein
                       organism = synthetic construct
SEQUENCE: 67
ASTWRGTSAG GNRLEKMEVT                                          20

SEQ ID NO: 68          moltype = AA   length = 20
FEATURE                Location/Qualifiers
REGION                 1..20
                       note = Synthetic construct
source                 1..20
                       mol_type = protein
                       organism = synthetic construct
SEQUENCE: 68
LSGTPERSGQ AVKVKLKAIP                                          20

SEQ ID NO: 69          moltype = AA   length = 20
FEATURE                Location/Qualifiers
REGION                 1..20
                       note = Synthetic construct
source                 1..20
                       mol_type = protein
                       organism = synthetic construct
SEQUENCE: 69
GAWEAVRDRI AEWGSWGIPS                                          20

SEQ ID NO: 70          moltype = AA   length = 20
FEATURE                Location/Qualifiers
REGION                 1..20
                       note = Synthetic construct
source                 1..20
                       mol_type = protein
                       organism = synthetic construct
SEQUENCE: 70
AMDMYSIEDR YFGGYAPEVG                                          20

SEQ ID NO: 71          moltype = AA   length = 11
FEATURE                Location/Qualifiers
REGION                 1..11
                       note = Synthetic construct
MOD_RES                1
                       note = ACETYLATION
SITE                   11
                       note = MISC_FEATURE - PEG11-C-NH2
source                 1..11
                       mol_type = protein
                       organism = synthetic construct
SEQUENCE: 71
YAAWPASGAW T                                                   11

SEQ ID NO: 72          moltype = AA   length = 15
FEATURE                Location/Qualifiers
REGION                 1..15
                       note = Synthetic construct
MOD_RES                1
                       note = ACETYLATION
SITE                   15
                       note = MISC_FEATURE - PEG11-C-NH2
source                 1..15
                       mol_type = protein
                       organism = synthetic construct
SEQUENCE: 72
LQWRRNFGVW ARYRL                                               15

SEQ ID NO: 73          moltype = AA   length = 10
FEATURE                Location/Qualifiers
REGION                 1..10
                       note = Synthetic construct
MOD_RES                1
                       note = ACETYLATION
```

-continued

```
SITE                     10
                         note = MISC_FEATURE - PEG11-YC-NH2
source                   1..10
                         mol_type = protein
                         organism = synthetic construct
SEQUENCE: 73
RGDLATLRQL                                                        10

SEQ ID NO: 74            moltype = AA  length = 11
FEATURE                  Location/Qualifiers
REGION                   1..11
                         note = Synthetic construct
MOD_RES                  1
                         note = ACETYLATION
MOD_RES                  1
                         note = D-Leucine
SITE                     11
                         note = MISC_FEATURE - PEG11-YC-NH2
source                   1..11
                         mol_type = protein
                         organism = synthetic construct
SEQUENCE: 74
LRGDLATLRQ L                                                      11

SEQ ID NO: 75            moltype = AA  length = 15
FEATURE                  Location/Qualifiers
REGION                   1..15
                         note = Synthtic construct
MOD_RES                  1
                         note = ACETYLATION
SITE                     15
                         note = MISC_FEATURE - PEG11-C-NH2
source                   1..15
                         mol_type = protein
                         organism = synthetic construct
SEQUENCE: 75
LQWRRNFGVW ARYRL                                                  15

SEQ ID NO: 76            moltype = AA  length = 10
FEATURE                  Location/Qualifiers
REGION                   1..10
                         note = Synthetic construct
MOD_RES                  1
                         note = ACETYLATION
SITE                     10
                         note = MISC_FEATURE - PEG11-C-NH2
source                   1..10
                         mol_type = protein
                         organism = synthetic construct
SEQUENCE: 76
FHAVPQSFYT                                                        10

SEQ ID NO: 77            moltype = AA  length = 10
FEATURE                  Location/Qualifiers
REGION                   1..10
                         note = Synthetic construct
MOD_RES                  1
                         note = ACETYLATION
SITE                     10
                         note = MISC_FEATURE - PEG11-C-NH2
source                   1..10
                         mol_type = protein
                         organism = synthetic construct
SEQUENCE: 77
FHAVPQSFYT                                                        10

SEQ ID NO: 78            moltype = AA  length = 9
FEATURE                  Location/Qualifiers
REGION                   1..9
                         note = Synthetic construct
source                   1..9
                         mol_type = protein
                         organism = synthetic construct
SEQUENCE: 78
FHAVPQSFY                                                         9

SEQ ID NO: 79            moltype = AA  length = 9
FEATURE                  Location/Qualifiers
REGION                   1..9
```

```
                             note = Synthetic construct
source                       1..9
                             mol_type = protein
                             organism = synthetic construct
SEQUENCE: 79
HAVPQSFYT                                                          9

SEQ ID NO: 80                moltype = AA  length = 10
FEATURE                      Location/Qualifiers
REGION                       1..10
                             note = Synthetic construct
MOD_RES                      1
                             note = ACETYLATION
source                       1..10
                             mol_type = protein
                             organism = synthetic construct
SEQUENCE: 80
FHAVPQSFYT                                                         10

SEQ ID NO: 81                moltype = AA  length = 11
FEATURE                      Location/Qualifiers
REGION                       1..11
                             note = Synthetic construct
MOD_RES                      1
                             note = ACETYLATION
MOD_RES                      1
                             note = D-Leucine
source                       1..11
                             mol_type = protein
                             organism = synthetic construct
SEQUENCE: 81
LRGDLATLRQ L                                                       11

SEQ ID NO: 82                moltype = AA  length = 11
FEATURE                      Location/Qualifiers
REGION                       1..11
                             note = Synthetic construct
MOD_RES                      1
                             note = ACETYLATION
source                       1..11
                             mol_type = protein
                             organism = synthetic construct
SEQUENCE: 82
YAAWPASGAW T                                                       11

SEQ ID NO: 83                moltype = AA  length = 20
FEATURE                      Location/Qualifiers
REGION                       1..20
                             note = Synthetic construct
MOD_RES                      1
                             note = ACETYLATION
source                       1..20
                             mol_type = protein
                             organism = synthetic construct
SEQUENCE: 83
LQWRRDDNVH NFGVWARYRL                                              20

SEQ ID NO: 84                moltype = AA  length = 11
FEATURE                      Location/Qualifiers
REGION                       1..11
                             note = Synthetic construct
MOD_RES                      1
                             note = ACETYLATION
source                       1..11
                             mol_type = protein
                             organism = synthetic construct
SEQUENCE: 84
KQYATPRVFW T                                                       11
```